United States Patent [19]
Chee et al.

[11] Patent Number: 5,861,242
[45] Date of Patent: *Jan. 19, 1999

[54] ARRAY OF NUCLEIC ACID PROBES ON BIOLOGICAL CHIPS FOR DIAGNOSIS OF HIV AND METHODS OF USING THE SAME

[75] Inventors: Mark Chee, Palo Alto; Thomas R. Gingeras, Santa Clara; Stephen P. A. Fodor, Palo Alto; Earl A. Hubble, Mountain View; MacDonald S. Morris, San Jose, all of Calif.

[73] Assignee: Affymetrix, Inc., Santa Clara, Calif.

[*] Notice: The term of this patent shall not extend beyond the expiration date of Pat. No. 5,837,832.

[21] Appl. No.: 781,550

[22] Filed: Jan. 9, 1997

Related U.S. Application Data

[63] Continuation of Ser. No. 284,064, Aug. 2, 1994, abandoned, which is a continuation-in-part of Ser. No. 143,312, Oct. 26, 1993, abandoned, which is a continuation-in-part of Ser. No. 82,937, Jun. 25, 1993, abandoned.

[51] Int. Cl.[6] ..................................................... C12Q 1/68
[52] U.S. Cl. ............................. 435/5; 422/50; 422/68.1; 435/6; 435/283.1; 435/810; 436/501; 536/23.1; 536/24.1; 536/24.3; 536/24.31; 536/24.32; 536/24.33; 935/77; 935/78
[58] Field of Search .................................... 435/5, 6, 283.1, 435/810; 436/501; 536/23.1, 24.1, 24.3–24.33; 935/77, 78; 422/50, 68.1

[56] References Cited

U.S. PATENT DOCUMENTS

| 4,656,127 | 4/1987 | Mundy | 435/6 |
|---|---|---|---|
| 4,683,195 | 7/1987 | Mullis et al. | 435/6 |
| 5,002,867 | 3/1991 | Macevicz | 435/6 |
| 5,143,854 | 9/1992 | Pirrung et al. | 436/518 |
| 5,202,231 | 4/1993 | Drmanac et al. | 435/6 |
| 5,273,632 | 12/1993 | Stockham et al. | 204/108.1 |
| 5,527,681 | 6/1996 | Holmes | 435/6 |

FOREIGN PATENT DOCUMENTS

| WO 89/10977 | 11/1989 | WIPO | C12Q 1/68 |
|---|---|---|---|
| WO 89/11548 | 11/1989 | WIPO | C12Q 1/68 |
| WO 90/00626 | 1/1990 | WIPO | C12Q 1/68 |
| WO 90/03382 | 4/1990 | WIPO | C07H 21/00 |
| WO 92/10092 | 6/1992 | WIPO | A01N 1/02 |
| WO 92/10588 | 6/1992 | WIPO | C12Q 1/68 |
| WO 93/17126 | 9/1993 | WIPO | C12Q 1/68 |
| WO 95/00530 | 1/1995 | WIPO | C07H 21/04 |

OTHER PUBLICATIONS

Elder, J.K., "Analysis of DNA oligonucleotide hybridization data by maximum entropy," *Maximum Entropy and Bayesian Methods*, pp. 1–10, Paris (1992).

(List continued on next page.)

*Primary Examiner*—Ardin H. Marschel
*Attorney, Agent, or Firm*—Townsend & Townsend & Crew LLP

[57] ABSTRACT

The invention provides an array of oligonucleotide probes immobilized on a solid support for analysis of a target sequence from a human immunodeficiency virus. The array comprises at least four sets of oligonucleotide probes 9 to 21 nucleotides in length. A first probe set has a probe corresponding to each nucleotide in a reference sequence from a human immunodeficiency virus. A probe is related to its corresponding nucleotide by being exactly complementary to a subsequence of the reference sequence that includes the corresponding nucleotide. Thus, each probe has a position, designated an interrogation position, that is occupied by a complementary nucleotide to the corresponding nucleotide. The three additional probe sets each have a corresponding probe for each probe in the first probe set. Thus, for each nucleotide in the reference sequence, there are four corresponding probes, one from each of the probe sets. The three corresponding probes in the three additional probe sets are identical to the corresponding probe from the first probe or a subsequence thereof that includes the interrogation position, except that the interrogation position is occupied by a different nucleotide in each of the four corresponding probes.

26 Claims, 19 Drawing Sheets

OTHER PUBLICATIONS

Hagstrom et al., "Maximum likelihood genetic sequence reconstruction from oligo content," Sep. 1992, Argonne Nat'l Laboratory Preprint MCS–P309–0592.

Lipshutz, Robert J., "Likelihood DNA sequencing by hybridization," *J. of Biomolecular Structure & Dynamics* 11:637–653 (1993).

Luo et al., "Cellular protein modulates effects of human immunodeficiency virus type 1 rev," *J. of Virology* 68:3850–3856 (1994).

Maxam et al., "A new method for sequencing DNA," *Proc. Natl. Acad.Sci. USA* (1977) 74:560–564.

Maxam et al., "Sequencing end–labeled DNA with base–specific chemical cleavages," *Methods in Enzymology* 65:499–560 (1980).

Querat et al., "Nucleotide sequence analysis of SA–OMVV, a Visna–related ovine lentivirus: phylogenetic history of lentiviruses," *Virology* 175:434–447 (1990).

Ratner et al., "Complete nucleotide sequence of the AIDS virus, HTLV–III," *Nature* 313:277–284 (1985).

Sambrook et al., Molecular Cloning, Cold Spring Harbor Laboratory Press, 1989, pp. 1145–1147.

Sanger et al., "DNA sequencing with chain–terminating inhibitors," *Proc. Natl. Acad. Sci. USA* (1977) 74:5463–5467.

Southern et al., "Analyzing and comparing nucleic acid sequences by hybridization to arrays of oligonucleotides: evaluation using experimental models," *Genomics* (1992) 13:1008–1017.

Stratagene 1988 Catalog, "Gene Characterization Kits," p. 39.

Wain–Hobson et al., "Nucleotide sequence of the AIDS virus, LAV," *Cell* 40:9–17 (1985).

```
5'Fluorescein-AAAGAAAAAAGACAGTACTAAATGGAGAAAAT  wildtype
PROBE 3'           tttttt•tgtcat                13mers
PROBE 3'          cttttttt•tgtcatg              15mers
PROBE 3'         tcttttttt•tgtcatga             17mers
PROBE 3'        ttctttttttt•tgtcatgat           19mers
5'Fluorescein-AAAGAAAAAAACAGTACTAAATGGAGAAAAT   mutant
```

FIG. 6

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:1:

GTAGAATTCT GTTGACTCAG ATTGG                      2 5

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:2:

AAATCCATAC AATACTCCAG TATTTGC                    2 7

( 2 ) INFORMATION FOR SEQ ID NO:3:

( i ) SEQUENCE CHARACTERISTICS:
        ( A ) LENGTH: 49 base pairs
        ( B ) TYPE: nucleic acid
        ( C ) STRANDEDNESS: single -continued ( D ) TOPOLOGY: linear ( i i ) MOLECULE TYPE: DNA (primer)

( x i ) SEQUENCE DESCRIPTION: SEQ ID NO:3:

AATTAACCCT CACTAAAGGG AGAGGAAGAA TCTGTTGACT CAGATTGGT 49

( 2 ) INFORMATION FOR SEQ ID NO:4:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:4:

AATTAACCCT CACTAAAGGG AGAAGTATAC TGCATTTTAC CATACCTAGT A 51

( 2 ) INFORMATION FOR SEQ ID NO:5:

( i ) SEQUENCE CHARACTERISTICS:
      ( A ) LENGTH: 48 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:5:

TAATACGACT CACTATAGGG AGATCGACGC AGGACTCGGC TTGCTGAA 48

( 2 ) INFORMATION FOR SEQ ID NO:6:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:6:

AATTAACCCT CACTAAAGGG AGACCTTGTA AGTCATTGGT CTTAAAGGTA 50

( 2 ) INFORMATION FOR SEQ ID NO:7:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:7:

GATAAGCTTG GGCCTTATCT ATTCCAT 27

( 2 ) INFORMATION FOR SEQ ID NO:8:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:8:

ACCCATCCAA AGGAATGGAG GTTCTTTC                                                             28

(2) INFORMATION FOR SEQ ID NO:9:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:9:

AATTTAATAC GACTCACTAT AGGGATTTCC CCACTAACTT CTGTATGTCA TTGACA        56

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:10:

AGCCTAGCTG AA                                                                              12

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:11:

TCGGATCGAC TT                                                                              12

(2) INFORMATION FOR SEQ ID NO:12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:12:

CGGAATTAAC CCTCACTAAA GGAATTAACC CTCACTAAAG GGAG                    44

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:13:

TAATACGACT CACTATAGGG AG                                                                   22

(2) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:14:

ATTTAGGTGA CACTATAGAA     20

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:15:

AAAGAAAAAA GACAGTACTA AATGGA     26

( 2 ) INFORMATION FOR SEQ ID NO:16:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:16:

TACTGTATTT TTT     13

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:17:

TACTGTCTTT TTT     13

( 2 ) INFORMATION FOR SEQ ID NO:18:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:18:

TACTGTGTTT TTT     13

( 2 ) INFORMATION FOR SEQ ID NO:19:

( i ) SEQUENCE CHARACTERISTICS:
        ( A ) LENGTH: 13 base pairs
        ( B ) TYPE: nucleic acid
        ( C ) STRANDEDNESS: single ( D ) TOPOLOGY: linear ( i i ) MOLECULE TYPE: DNA (oligonucleotide)

( x i ) SEQUENCE DESCRIPTION: SEQ ID NO:19:

TACTGTTTTT TTT                                                              13

( 2 ) INFORMATION FOR SEQ ID NO:20:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:20:

GTACTGACTT TTT                                                              13

( 2 ) INFORMATION FOR SEQ ID NO:21:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:21:

GTACTGCCTT TTT                                                              13

( 2 ) INFORMATION FOR SEQ ID NO:22:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:22:

GTACTGGCTT TTT                                                              13

( 2 ) INFORMATION FOR SEQ ID NO:23:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:23:

GTACTGTCTT TTT                                                              13

( 2 ) INFORMATION FOR SEQ ID NO:24:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:24:

AGTACTAGCT TTT    13

( 2 ) INFORMATION FOR SEQ ID NO:25:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:25:

AGTACTCGCT TTT    13

( 2 ) INFORMATION FOR SEQ ID NO:26:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:26:

AGTACTGGCT TTT    13

( 2 ) INFORMATION FOR SEQ ID NO:27:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:27:

AGTACTTGCT TTT    13

( 2 ) INFORMATION FOR SEQ ID NO:28:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:28:

TAAAGTAAGA CATAAC    16

( 2 ) INFORMATION FOR SEQ ID NO:29:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:29:

GGCTGACGTC AGCAAT    16

( 2 ) INFORMATION FOR SEQ ID NO:30:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (oligonucleotide)

( x i ) SEQUENCE DESCRIPTION: SEQ ID NO:30:

TTGCTGACAT CAGCC 15

( 2 ) INFORMATION FOR SEQ ID NO:31:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:31:

TTGCTGACCT CAGCC 15

( 2 ) INFORMATION FOR SEQ ID NO:32:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:32:

TTGCTGACGT CAGCC 15

( 2 ) INFORMATION FOR SEQ ID NO:33:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:33:

TTGCTGACTT CAGCC 15

( 2 ) INFORMATION FOR SEQ ID NO:34:

( i ) SEQUENCE CHARACTERISTICS:
    ( A ) LENGTH: 831 base pairs
    ( B ) TYPE: nucleic acid
    ( C ) STRANDEDNESS: single
    ( D ) TOPOLOGY: linear ( i i ) MOLECULE TYPE: DNA (oligonucleotide)

( x i ) SEQUENCE DESCRIPTION: SEQ ID NO:34:

GGAAGAAATC TGTTGACTCA GATTGGTTGT ACTTTAAATT TCCCCATTAG TCCTATTGAA 60

ACTGTACCAG TAAAATTAAA GCCAGGAATG GATGGCCCAA AAGTTAAGCA ATGGCCATTG 120

ACAGAAGAAA AAATAAAAGC ATTAGTAGAG ATATGTACAG AAATGGAAAA GGAAGGGAAA 180

ATTTCAAAAA TTGGGCCTGA AAATCCATAC AATACTCCAG TATTTGCTAT AAAGAAAAAA 240

GACAGTACTA AATGGAGAAA ACTAGTAGAT TTCAGAGAAC TTAATAAAAG AACTCAAGAC 300

| TTCTGGGAAG | TTCAGTTAGG | AATACCACAC | CCCGCAGGGT | TAAAAAGAA | AAAATCAGTA | 360 |
| ACAGTATTGG | ATGTGGGTGA | TGCATACTTT | TCAGTTCCCT | TAGATAAAGA | CTTTAGAAAG | 420 |
| TATACTGCAT | TTACCATACC | TAGTATAAAC | AATGAGACAC | CAGGGATTAG | ATATCAGTAC | 480 |
| AATGTGCTGC | CACAGGGATG | GAAAGGATCA | CCAGCAATAT | TCCAAAGTAG | CATGACAAAA | 540 |
| ATCTTAGAGC | CTTTTAGAAA | ACAGAATCCA | GACATAGTTA | TCTATCAATA | CATGGATGAT | 600 |
| TTGTATGTAG | GATCTGACTT | AGAAATAGGG | CAGCATAGAA | CAAAATAGA | GGAACTGAGA | 660 |
| CAGCATCTGT | TGAGGTGGGG | ATTTACCACA | CCAGACAAAA | AACATCAGAA | AGAACCTCCA | 720 |
| TTCCTTTGGA | TGGGTTATGA | ACTCCATCCT | GATAAATGGA | CAGTACAGCC | TATAATGCTG | 780 |
| CCAGAAAAAG | ACAGCTGGAC | TGTCAATGAC | ATACAGAAGT | TAGTGGGAAA | A | 831 |

( 2 ) INFORMATION FOR SEQ ID NO:35:

( i ) SEQUENCE CHARACTERISTICS:
        ( A ) LENGTH: 831 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:35:

| GGRAGAAATN | NNNNNTCTCA | GATTGGTTGT | NNNNBCNNNN | NNNNNNNNN | NNNNTNNNN | 60 |
| ACTGNNNCAG | NNNNNNAAAA | GCCAGGGAGG | GATGGCCNNN | NAGTTAAGCA | ANNNNCNTTG | 120 |
| ACAGAAGAAA | ANATAAAAGC | ATTAGTAGAG | ATATGTASAG | AAAGGGAAAA | GGAAGGGAAA | 180 |
| ANNNNNNNAA | TTGGGCCTGA | AANTCNNGNN | NNNACNNNNN | NNNNNNNNNT | AANNGAAAAA | 240 |
| GACAGTANTA | AATGGAGAAA | ACTAGNAGAT | TTCAGAGAAC | NNNNNNRAAG | AACTCANNNN | 300 |
| TTCTGGGAAG | TTCAGTTAGG | AATACCACAC | NCNNNGGGT | TAAAGAGNRA | AAAATCAGTA | 360 |
| ACAGTATTGG | ATGTGGGTGA | TGCNNNNNNN | NNNNNNNCN | NNGATAAANN | NNNTNNNNAG | 420 |
| TATACNNNAT | TNACNNTACC | NNNTNNNNAC | AATGAGACAC | CAGGGATTAG | NNNTCAGTAC | 480 |
| AATGTGCTGC | CACAGGGATG | GAAGGGATCA | CCAGCAATNN | NNNAAAGTAG | CATGACARNN | 540 |
| NNCTTAGAGN | CTTNNNNAAA | ACAGAATCCA | GACATANNNN | NNNNNNNNA | CAGGGATGAT | 600 |
| TNNTATGTAG | GATCTGACNT | AGAAATAGGG | CAGCATAGAA | GAAAATAGA | GGAACTGAGA | 660 |
| CAGCANCTGT | TGAGGTGGGG | ATTTACCACA | CCAGACAAAA | NACATCAGAA | AGAACCNNNN | 720 |
| NNNNNNNGGA | TGGGTTATGA | NNTCNNNNNN | NNNNAATGGA | CAGTACAGNN | NNNNNTGCTG | 780 |
| CCAGRARARG | ACAGCTNNAC | TGTNNNNGAC | ATACAGAAGT | TAGTGGGGRA | A | 831 |

( 2 ) INFORMATION FOR SEQ ID NO:36:

( i ) SEQUENCE CHARACTERISTICS:
        ( A ) LENGTH: 831 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:36:

| GGRAGAAATN | NNNNNCTCA | GATTGGTTGT | ACNNNNNNNN | NNNNNNTNNN | NNCTATTGAA | 60 |
| ACTGTNCCAG | TAAATAAAA | GCCAGGRAGG | GAWGGCCCAA | AAGTTAAGCA | AWNNCNATTG | 120 |
| ACAGAAGAAA | AAATAAAAGC | ATTAGTAGAG | ATATGTACAG | AAAGGGAAAR | GGAAGGGAAA | 180 |
| AGNNNNNAAA | TTGGGCCTGA | AAATCCAGAN | ANTACTNNNG | TATTNNCTAT | AAAGRAAAAA | 240 |

```
GACAGTACTA  AATGGAGAAA  ACTAGTAGAT  TTCAGAGAAC  TTANNAAAAG  AACTCAANAC      300

TTCTGGGAAG  TTCAGTTAGG  AATACCACAC  CCCNCNGGGT  TAAAGAGGAA  AAAATCAGTA      360

ACAGTATTGG  ATGTGGGTGA  TGCANNNNN   NNNNNCCCT   TAGATAAAGA  CTTTAGNAAG      420

TATACTGCAT  TTACCATACC  NNGTATAAAC  AATGAGACAC  CAGGGATTAG  ATATCAGTAC      480

AATGTGCTGC  CACAGGGATG  GAARGGATCA  CCAGCAATAT  TCCAAAGTAG  CATGACAAAA      540

ATCTTAGAGC  CTTTTAGAAA  ACAGAATCCA  GACATAGTNN  NNNNNNNATA  CAKGGATGAT      600

TTGTATGTAG  GATCTGACTT  AGAAATAGGG  CAGCATAGAA  GAAAATAGA   GGAACTGAGA      660

CAGCATCTGT  TGAGGTGGGG  ATTTACCACA  CCAGACAAAA  AACATCAGAA  AGAACCTCNN      720

NNNNNNTGGA  TGGGTTATGA  ACTCCANNNN  NNNAAATGGA  CAGTACAGCC  NNNNATGCTV      780

CCAGAAAAAG  ACAGCTGNAC  TGTCNNNNAC  ATACAGAAGT  TAGTGGGGAG  A               831
```

( 2 ) INFORMATION FOR SEQ ID NO:37:

( i ) SEQUENCE CHARACTERISTICS:
        ( A ) LENGTH: 831 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:37:

```
GGRAGGAATC  TGTTNNCTCA  GATTGGTTGT  ACTNNNNNNN  NNNCCATTNN  TCCTATTGAA       60

ACTGTACCAG  KAAAATAAAA  GCCAGGAAGG  GATGGCCCAA  AAGTTAAGCA  ATGRCBMWTG      120

ACAGAAGAAA  AAATAAAAGC  ATTAGTAGAG  ATATGTACAG  AAAGGGAAAR  GGAAGGGAAA      180

AKTNNNAAAA  TTGGGCCTGA  AAATCCAGAC  AATACTCNNG  TATTTGCTAT  AAAGAAAAAA      240

GACAGTACTA  AATGGAGAAA  ACTAGTAGAT  TTCAGAGAAC  TTAATAAAAG  AACTCAAGAC      300

TTCTGGGAAG  TTCAGTTAGG  AATACCACAC  CCCNNAGGGT  TAAARAGGAA  AAAATCAGTA      360

ACAGTATTGG  ATGTGGGTGA  TGCATNNNTT  CSNNNTCCCT  TAGATAAAGA  CTTTAGAAAG      420

TATACTGCAT  TTACCATACC  TAGTATAAAC  AATGAGACAC  CAGGGATTAG  ATATCAGTAC      480

AATGTGCTGC  CACAGGGATG  GAAAGGATCA  CCAGCAATAT  TCCAAAGTAG  CATGACAAAA      540

ATCTTAGAGC  CTTTTAGAAA  ACAGAATCCA  GACATAGTTA  TNTNTCAATA  CATGGATGAT      600

TTGTATGTAG  GATCTGACTT  AGAAATAGGG  CAGCATAGAA  CAAAATAGA   GGAACTGAGA      660

CAGCATCTGT  TGAGGTGGGG  ATTTACCACA  CCAGACAAAA  AACATCAGAA  AGAACCTCCN      720

NNNNNNTGGA  TGGGTTATGA  ACTCCATNNN  NNTAAATGGA  CAGTACAGCC  TNNNATGCTA      780

CCAGAARAAG  ACAGCTGGAC  TGTCAANGAC  ATACAGAAGT  TAGTGGGGRG  A               831
```

( 2 ) INFORMATION FOR SEQ ID NO:38:

( i ) SEQUENCE CHARACTERISTICS:
        ( A ) LENGTH: 831 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:38:

```
GGAAGAAATC  TGTTGACTCA  GATTGGTTGT  ACTTTAAANN  NNCCCATTAG  TCCTATTGAA       60

ACTGTACCAG  TAAAATWAAA  GCCAGGAAKG  GATGGCCCAA  AAGTTAAGCA  ATGRMVGATG      120

ACAGAAGAAA  AAATAAAAGC  ATTAGTAGAG  ATATGTACAG  AAADGGAAAR  GGAAGGGAAA      180
```

| | | | | | |
|---|---|---|---|---|---|
| AKTTCAAAAA | TTGGGCCTGA | AAATCCAKAC | AATACTCCAG | TATTTGCTAT | AAAGAAAAA | 240 |
| GACAGTACTA | AATGGAGAAA | ACTAGTAGAT | TTCAGAGAAC | TTAATAAAAG | AACTCAAGAC | 300 |
| TTCTGGGAAG | TTCAGTTAGG | AATACCACAC | CCCGCNGGGT | TAAARAAGAA | AAAATCAGTA | 360 |
| ACAGTATTGG | ATGTGGGTGA | TGCATACNNN | NNNNNTCCCT | TAGATAAAGA | CTTTAGAAAG | 420 |
| TATACTGCAT | TTACCATACC | TAGTATAAAC | AATGAGACAC | CAGGGATTAG | ATATCAGTAC | 480 |
| AATGTGCTGC | CACAGGGATG | GAAAGGATCA | CCAGCAATAT | TCCAAAGTAG | CATGACAAAA | 540 |
| ATCTTAGAGC | CTTTTAGAAA | ACAGAATCCA | GACATAGTTA | TCTATCAATA | CATGGATGAT | 600 |
| TTGTATGTAG | GATCTGACTT | AGAAATAGGG | CAGCATAGAA | CAAAAATAGA | GGAACTGAGA | 660 |
| CAGCATCTGT | TGAGGTGGGG | ATTTACCACA | CCAGACAAAA | AACATCAGAA | AGAACCTCCN | 720 |
| NNNNTTGGA | TGGGTTATGA | ACTCCATCNN | NATAAATGGA | CAGTACAGCC | TANNATGCTG | 780 |
| CCAGAAAAAG | ACAGCTGGAC | TGTCAATGAC | ATACAGAAGT | TAGTGGGGGG | A | 831 |

(2) INFORMATION FOR SEQ ID NO:39:

(i) SEQUENCE CHARACTERISTICS:
(A) LENGTH: 831 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:39:

| | | | | | |
|---|---|---|---|---|---|
| NGAAGAAANC | TNNNNCTCA | GATTGNNNC | NNNNNNNNN | NNNNNNNNN | CNNNNNNNG | 60 |
| NCTGNNNCAG | TANNATAAAA | GCCAGGAAGG | GATGGCCCAA | ANNNNNNNGN | NNNNNNNTTG | 120 |
| ACAGAAGAAA | AAATAAAAGC | ATTAGGGGRG | NNNNNGNSAG | RGGGGAAAA | GGAAGGGAAA | 180 |
| AGNNNNNNAA | TTGGGCCTGA | AAATCNNGAC | NANACNNNNN | TNNNNNCNN | NNGGGGRAAG | 240 |
| AACNNNNTA | GAKGGRGAGA | ATNNNNNAT | TTCAGAGAAC | TNNNNGGNN | NACTCAAGNC | 300 |
| TTCDGGGAAG | TTNNANGNGG | AATACCNNNN | NNNNNGGGT | TAAAGGGGRA | AAAATCAGTA | 360 |
| ANNNNCNGG | AGGTGGGTGA | TGCNNNNNN | NNNNNNNCN | NNNNDGRNNN | NNNNNNNN | 420 |
| NNNNNNAT | TNACNNTACC | NNNTNNNAAC | AATGAGACAC | CAGGGATTAG | ATATCAGTAC | 480 |
| AATNNNNNN | NACAGGGATG | GAAGGGATCA | CCAGCAATNN | NNNAAAGTAG | CATGACAAAA | 540 |
| NNCTTAGAGC | CTTNNANNGG | NGNANNGCCA | GACATAGNNN | NNNNNNNTA | CATGGATGAT | 600 |
| TTNTATGTAG | GATCTGACTT | AGAAATAGGG | CAGCATAGAA | GAAAATAGA | GGAGCTGAGG | 660 |
| GAANNNNGT | TGAGGTGGGG | RCCNNNNAGA | CCAGAACGNG | NACATCAGAA | AGAACCTCNN | 720 |
| NNNNNNGGA | TGGGTTATGA | NCTCCNTNNN | NNTAAATGGA | CAGTACAGCN | NNNNNNCTG | 780 |
| CCAGRARARG | ACAGCTGGAC | TGTCNNNGAC | ATACAGAAGT | TAGKGGGGAA | A | 831 |

(2) INFORMATION FOR SEQ ID NO:40:

(i) SEQUENCE CHARACTERISTICS:
(A) LENGTH: 830 base pairs
(B) TYPE: nucleic acid
(C) STRANDEDNESS: single
(D) TOPOLOGY: linear (ii) MOLECULE TYPE: DNA (oligonucleotide)

(xi) SEQUENCE DESCRIPTION: SEQ ID NO:40:

| | | | | | |
|---|---|---|---|---|---|
| GGRAGAAATC | TGTTGACTCA | GATTGGTTNC | NNNNNNNNN | NNNNNNNN | CNNNNNNAG | 60 |
| ACTGTNCCAG | TAAAATAAAA | GCCAGGAAGG | GATGGCCCAA | ANNNNNAGN | NNNNNATTG | 120 |

```
ACAGAAGAAA AAATAAAAGC ATTAGTAGRR ANNGGACAGR GRGGGAAARG GAAGGGAAAA      180
GTNNNNAAAT TGGGCCTGAA AATCCAGACA ATACTNNNGT NNNNNCNNN  ARGGARAAGA      240
ACANNNCTAG ATGGAGAAAA TTANNNGATT TCAGAGAACT TNNNNNGAGA ACTCAAGACT      300
TCTGGGAAGT TCNATGAGGA ATACCANNTC MNNNNGGGTT AAAGAGGAAA AAATCAGTAA      360
CNNTNCTGGA KGTGGGTGAT GCANNNNNN  NNNTCCCTN  NNATGANNNN NNNNNNNNNN     420
NNNNNCATT  TACCATACCT NGTATAAACA ATGAGACACC AGGGATTAGA TATCAGTACA      480
ATGNNNNTCC ACAGGGATGG AAGGGATCAC CAGCAATATT CCAAAGTAGC ATGACAAAAA      540
TCTTAGAGCC TTTTANNGGV VAAAAGCCAG ACATAGTTNN NTANNNATAC ATGGATGATT      600
TGTATGTAGG ATCTGACTTA GAAATAGGGC AGCATAGAAG AAAAATAGAG GAGCTGAGRS      660
AMCNNNTGTT GAGGTGGGGA CCNNNGNSAC CAGAMCVAAA ACATCAGAAA GAACCTCCNN      720
NNNNNTGGAT GGGTTATGAA CTCCATCCTG NTAAATGGAC AGTACAGCCN NNNGNGCTGC      780
CAGAAAAAGA VAGCTGGACT GTCANTGACA KACAGAAGTT AGKGGGGAAA                 830
```

( 2 ) INFORMATION FOR SEQ ID NO:41:

( i ) SEQUENCE CHARACTERISTICS:
        ( A ) LENGTH: 827 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:41:

```
GGAAGAAATC TGTTGACTCA GATTGGTTSC ACNNNNNNNN NNNNNNNNNN CNNNNNNNAG      60
ACTGTACCAG KAAAATAAAA GCCAGGAAGG GAWGGCCCAA AAGNNNAASN NNNANTAWTG     120
ACAGAAGRAA AAATAAAAGC ATTAGTAGAA AATGGGACAG RGRGGGAAAR GGAAGGGAAA     180
GTTNNAAAAT TGGGCCTGAA AATCCAGACA ATACTCNNGT NNNNNCNNG  AGGGAAAAGA     240
ACAGHACTAG ATGGAGAAAA TTAGNAGATT TCAGAGAACT TAATAAGAGA ACTCAAGACT     300
TCTGGGAAGT TCAATKAGGA ATACCACATC CNCNGGGTTA AARARGAAAA AATCAGTAAC     360
AGTACTGGAK GTGGGTGATG CADNTNNNNN NNTTCCCTTA GATGAANNNN NCNNNNNAGA     420
TANNGCATTT ACCATACCTA GTATAAACAA TGAGACACCA GGGATTAGAT ATCAGTACAA     480
TGTNNTTMCA CAGRGATGGA ARGGATCACC AGCAATATTC CAAAGTAGCA TGACAAAAAT     540
CTTAGAGCCT TTTAGARRAC AAAAKCCAGA CATAGTTATC TATCAATACA TGGATGATTT     600
GTATGTAGGA TCTGACTTAG AAATAGGGSA GCATAGAASA AAAATAGAGG AGCTGAGRCA     660
ACANCTGTTG AGGTGGGGCV VGGACACCAG AMCMAAAACA TCAGAAAGAA CCTCCNNNN      720
NTTGGATGGG TTATGAACTC CATNCNGATA AATGGACAGT ACAGCCTNNN GNGCTGCCAG     780
AARAAGACAG CTGGACTGTC AANGACATAC AGAAGTTAGT GGGGAAA                   827
```

( 2 ) INFORMATION FOR SEQ ID NO:42:

( i ) SEQUENCE CHARACTERISTICS:
        ( A ) LENGTH: 825 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:42:

```
GGAAGAAATC TGTTGACTCA GATTGGTTSC MCTNNNNNNN NNNNNNNNNN CNNNNTTGAG      60
```

| | | | | | | |
|---|---|---|---|---|---|---|
|ACTGTACCAG|TAAAAWAAAA|GCCAGGAAKG|GAWGGCCCAA|AAGTNAAASN|NNNAMMRDTG|120|
|ACAGAAGAAA|AAATAAAAGC|ATTAGTAGAA|AATKGGACAG|RGRGGGAAAR|GGAAGGGRAA|180|
|ADTCAAAAAT|TGGGCCTGAA|AATCCAKACA|ATACTCCANT|ATNTGCCMGG|ARGGAAAARA|240|
|ACAGYACTAG|ATGGAGAAAA|TTAGTAGATT|TCAGAGAACT|TAATAAGAGA|ACTCAAGACT|300|
|TCTGGGAAGT|TCAATTAGGA|ATACCACATC|CGCNGGGTTA|AARAAGAAAA|AATCAGTAAC|360|
|AGTACTGGAT|GTGGGTGATG|CADATNNNNN|NNNTCCCTTA|GATGAAGANW|NCNNNNNAKA|420|
|TACTGCATTT|ACCATACCTA|GTATAAACAA|TGAGACACCA|GGGATTAGAT|ATCAGTACAA|480|
|TGTGCTTHCA|CAGGGATGGA|RGGATCACCA|GCAATATTCC|AAAGTAGCAT|GACAAAAATC|540|
|TTAGAGCCTT|TTAGAAAACA|AAAKCCAGAC|ATAGTTATCT|ATCAATACAT|GGATGATTTG|600|
|TATGTAGGAT|CTGACTTAGA|AATAGGGSAG|CATAGAACAA|AAATAGAGGA|GCTGAGACAA|660|
|CATCTGTTGA|GGTGGGGCCT|GACACCAGAM|CMAAAACATC|AGAAAGAACC|TCCATNNNTT|720|
|TGGATGGGTT|ATGAACTCCA|TCNNNATAAA|TGGACAGTAC|AGCCTANNGT|GCTGCCAGAA|780|
|AAAGACAGCT|GGACTGTCAA|TGACATACAG|AAGTTAGKGG|GGAAA| |825|

( 2 ) INFORMATION FOR SEQ ID NO:43:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:43:

AAAGAAAAAA GACAGTACTA AATGGAGAAA AT          32

( 2 ) INFORMATION FOR SEQ ID NO:44:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:44:

TACTGTTTTT TT          12

( 2 ) INFORMATION FOR SEQ ID NO:45:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:45:

GTACTGTTTT TTTC          14

( 2 ) INFORMATION FOR SEQ ID NO:46:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (i i) MOLECULE TYPE: DNA (oligonucleotide)

(x i) SEQUENCE DESCRIPTION: SEQ ID NO:46:

AGTACTGTTT TTTTCT 16

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (oligonucleotide)

(x i) SEQUENCE DESCRIPTION: SEQ ID NO:47:

TAGTACTGTT TTTTTCTT 18

(2) INFORMATION FOR SEQ ID NO:48:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (oligonucleotide)

(x i) SEQUENCE DESCRIPTION: SEQ ID NO:48:

AAAGAAAAAA AACAGTACTA AATGGAGAAA AT 32

ARRAY OF NUCLEIC ACID PROBES ON BIOLOGICAL CHIPS FOR DIAGNOSIS OF HIV AND METHODS OF USING THE SAME

CROSS-REFERENCE TO RELATED APPLICATION

This is a continuation of application Ser. No. 08/284,064, filed Aug. 2, 1994, now abandoned, the disclosure of which is incorporated by reference, which is a continuation-in-part of 08/143,312, filed Oct. 26, 1993, now abandoned, which is a continuation in part of U.S. patent application Ser. No. 08/082,937, filed June 25, 1993, now abandoned, each of which is incorporated by reference in its entirety for all purposes.

Research leading to the invention was funded in part by NIH grant No. 1R01HG00813-01 and DOE grant No. DE-FG03-92-ER81275, and the government may have certain rights to the invention.

BACKGROUND OF THE INVENTION

1. Field of the Invention

The present invention provides arrays of oligonucleotide probes immobilized in microfabricated patterns on silica chips for analyzing molecular interactions of biological interest. The chips are employed for diagnoses useful in the rational therapeutic management of AIDS patients.

2. Description of Related Art

Oligonucleotide probes have long been used to detect complementary nucleic acid sequences in a nucleic acid of interest (the "target" nucleic acid). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid. See, e.g., PCT patent publication Nos. WO 89/10977 and 89/11548. Others have proposed the use of large numbers of oligonucleotide probes to provide the complete nucleic acid sequence of a target nucleic but failed to provide an enabling method for using arrays of immobilized probes for this purpose. See U.S. Pat. Nos. 5,202,231 and 5,002,867 and PCT patent publication No. WO 93/17126.

The development of VLSIPS™ technology has provided methods for making very large arrays of oligonucleotide probes in very small areas. See U.S. Pat. No. 5,143,854 and PCT patent publication Nos. WO 90/15070 and 92/10092, each of which is incorporated herein by reference in its entirety for all purposes. U.S. patent application Serial No. 08/082,937, filed Jun. 25, 1993, describes methods for making arrays of oligonucleotide probes that can be used to provide the complete sequence of a target nucleic acid and to detect the presence of a nucleic acid containing a specific nucleotide sequence.

Microfabricated arrays of large numbers of oligonucleotide probes, called "DNA chips" offer great promise for a wide variety of applications. The present invention provides inter alia suitable chips and methods for analyzing human immunodeficiency virus strains and coparasitizing microorganisms.

SUMMARY OF THE INVENTION

The invention provides an array of oligonucleotide probes immobilized on a solid support for analysis of a target sequence from a human immunodeficiency virus. The array comprises at least four sets of oligonucleotide probes 9 to 21 nucleotides in length. A first probe set has a probe corresponding to each nucleotide in a reference sequence from a human immunodeficiency virus. A probe is related to its corresponding nucleotide by being exactly complementary to a subsequence of the reference sequence that includes the corresponding nucleotide. Thus, each probe has a position, designated an interrogation position, that is occupied by a complementary nucleotide to the corresponding nucleotide. The three additional probe sets each have a corresponding probe for each probe in the first probe set. Thus, for each nucleotide in the reference sequence, there are four corresponding probes, one from each of the probe sets. The three corresponding probes in the three additional probe sets are identical to the corresponding probe from the first probe or a subsequence thereof that includes the interrogation position, except that the interrogation position is occupied by a different nucleotide in each of the four corresponding probes.

The reference sequence is often the reverse transcriptase gene of the human immunodeficiency virus, in which case, the reference sequence is often a full-length or substantially full-length reverse transcriptase sequence. For analysis of a full-length or substantially full-length reverse transcriptase sequence, a chip typically comprises at least 3200 probes (four probes for each nucleotide in the reference sequence). However, the chip often comprises 10,000 or more probes.

Some arrays have fifth, sixth, seventh and eighth probe sets. The probes in each set are selected by analogous principles to those for the probes in the first four probe sets, except that the probes in the fifth, sixth, seventh and eighth sets exhibit complementarity to a second reference sequence. In some chips, the reference sequence is from the coding strand of a reverse transcriptase gene and the second reference sequence from the noncoding strand. Alternatively, the second reference sequence can be a subsequence of the first reference sequence having a substitution of at least one nucleotide. In a further variation, the second reference sequence is from a 16S RNA (or genomic DNA encoding the RNA) from a pathogenic microorganism.

In another aspect, the invention provides methods for comparing a target nucleic acid from a human immunodeficiency virus with a reference sequence from a second human immunodeficiency virus having a predetermined sequence of nucleotides. The target nucleic acid is hybridized to an array of oligonucleotide probes as described above. The relative specific binding of the probes in the array to the target is determined to indicate whether the target sequence is the same or different from the reference sequence.

In some applications, the target sequence has a substituted nucleotide relative to the reference sequence in at least one undetermined position, and the relative specific binding of the probes indicates the location of the position and the nucleotide occupying the position in the target sequence. In some applications the target sequence has a substituted nucleotide relative to the reference sequence in at least one position, the substitution conferring drug resistance to the human immunodeficiency virus, and the relative specific binding of the probes reveals the substitution.

BRIEF DESCRIPTION OF THE DRAWINGS

FIG. 5 (SEQ ID NOS. 34 through 42): Sequence read from HV 407 chip hybridized to pPol19 and HXB2 (separate experiments). The reference sequence is designated "wildtype." Beneath the reference sequence are four rows of sequence read from the chip hybridized to the pPol19 target, the first row being read from 13 mers, the second row from 15 mers, the third row from 17 mers and the fourth row from 19 mers. Beneath these sequences, there are four further rows of sequence read from the chip hybridized to the HXB2 target. Successive rows are read from 13 mers, 15 mers, 17 mers and 19 mers. Each nucleotide in a row is called from the relative fluorescence intensities of probes in A-, C-, G- and T-lanes. Regions of ambiguous sequence read from the chip are highlighted. The strain differences between the HBX2 sequence and the reference sequence that were correctly detected are indicated (*), and those that could not be called are indicated (o). (The nucleotide at position 417 was read correctly in some experiments). The location of some mutations known to be associated with drug resistance that occur in readable regions of the chip are shown above (codon number) and below (mutant nucleotide) the sequence designated "wildtype." The locations of primer used to amplify the target sequence are indicated by arrows.

FIG. 6 (SEQ ID NOS. 43 through 48): Detection of mixed target sequences. The mutant target differs from the wildtype by a single mutation in codon 67 of the reverse transcriptase gene. Each different sized group of probes has a column of four probes for reading the nucleotide in which the mutation occurs. The four probes occupying a column are represented by a single probe in the Figure with the symbol (o) indicating the interrogation position, which is occupied by a different nucleotide in each probe.

DETAILED DESCRIPTION

Figure 1A:
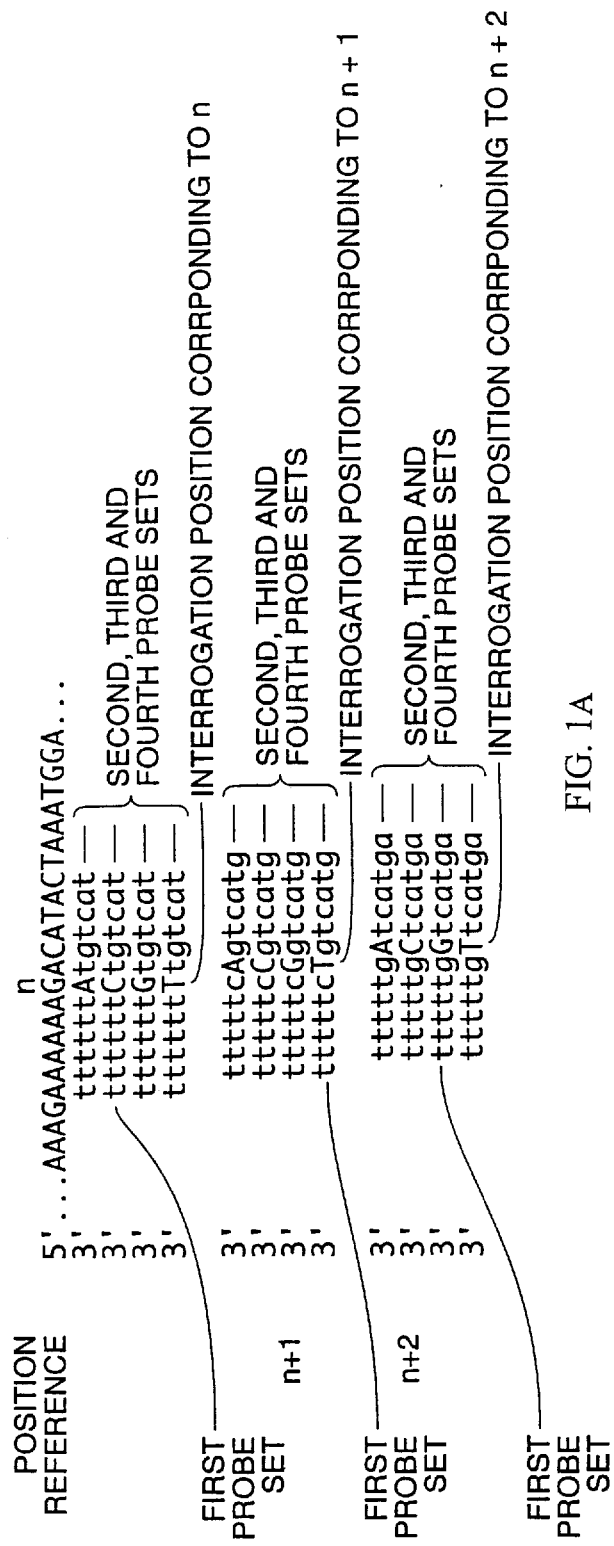
FIG. 1 (SEQ ID NOS. 17 through 27): Tiling strategy for analysis of a HIV reverse transcriptase target gene. The Figure shows three successive columns, each containing four probes (13 mers). The interrogation position in each probe is capitalized. For analysis of the full-length reverse transcriptase gene, the chip contains at least 857 total columns each having four probes.

HIV has infected a large and expanding number of people, resulting in massive health care expenditures. HIV can rapidly become resistant to drugs used to treat the infection, primarily due to the action of the heterodimeric protein (51 kDa and 66 kDa) HIV reverse transcriptase (RT) both subunits or which are encoded by the 1.7 kb pol gene. The high error rate (5–10 per round) of the RT protein is believed to account for the hypermutability of HIV. The nucleoside analogues, i.e., AZT, ddI, ddC, and d4T, commonly used to treat HIV infection are converted to nucleotide analogues by sequential phosphorylation in the cytoplasm of infected cells, where incorporation of the analogue into the viral DNA results in termination of viral replication, because the 5'→3' phosphodiester linkage cannot be completed. However, after about 6 months to 1 year of treatment or less, HIV typically mutates the RT gene so as to become incapable of incorporating the analogue and so resistant to treatment. Several mutations known to be associated with drug resistance are shown in the table below. After a virus acquires drug resistance via a mutation, the patient suffers dramatically increased viral load, worsening symptoms (typically more frequent and difficult-to-treat infections), and ultimately death. Switching to a different treatment regimen as soon as a resistant mutant virus takes hold may be an important step in patient management which prolongs patient life and reduces morbidity during life.

TABLE 1

RT MUTATIONS ASSOCIATED WITH DRUG RESISTANCE

| ANTIVIRAL | CODON | aa CHANGE | nt CHANGE |
|---|---|---|---|
| AZT | 67 | Asp → Asn | GAC → AAC |
| AZT | 70 | Lys → Arg | AAA → AGA |
| AZT | 215 | Thr → Phe or Tyr | ACC → TTC or TAC |
| AZT | 219 | Lys → Gln or Glu | AAA → CAA or GAA |
| AZT | 41 | Met → Leu | ATG → TTG or CTG |
| ddI and ddC | 184 | Met → Val | ATG → GTG |
| ddI and ddC | 74 | Leu → Val | |
| TIBO 82150 | 100 | Leu → Ile | |
| ddC | 65 | Lys → Asn | AAA → AGA |
| ddC | 69 | Thr → Asp | ACT → GAT |
| 3TC | 184 | Met → Val | ATG → GTG or GTA |
| 3TC | 184 | Met → Ile | ATG → ATA |
| AZT + ddI | 62 | Ala → Val | GCC → GTC |
| AZT + ddI | 75 | Val → Ile | GTA → ATA |
| AZT + ddI | 77 | Phe → Leu | TTC → TTA |
| AZT + ddI | 116 | Phe → Tyn | TTT → TAT |
| AZT + ddI | 151 | Gln → Met | CAG → ATG |
| Nevaripine | 103 | Lys → Asn | AAA → AAT |
| | 106 | Val → Ala | GTA → GCA |

TABLE 1-continued

RT MUTATIONS ASSOCIATED WITH DRUG RESISTANCE

| ANTIVIRAL | CODON | aa CHANGE | nt CHANGE |
|---|---|---|---|
| | 108 | | |
| | 181 | Tyr → Cys | TAT → TGT |
| | 188 | Tyr → His | TAT → CAT |
| | 190 | Gly → Ala | GGA → GCA |

N.B. Other mutations confer resistance to other drugs.

In addition to being infected with HIV, AIDS patients are often also infected with a wide variety of other infectious agents giving rise to a complex series of symptoms. Often diagnosis and treatment is difficult because many different pathogens (some life-threatening, others routine) cause similar symptoms. Some of these infections, so-called opportunistic infections, are caused by bacterial, fungal, protozoan or viral pathogens which are normally present in small quantity in the body, but are held in check by the immune system. When the immune system in AIDS patients fails, these normally latent pathogens can grow and generate rampant infection. In treating such patients, it would be desirable simultaneously to diagnose the presence or absence of a variety of the most lethal common infections, determine the most effective therapeutic regime against the HIV virus, and monitor the overall status of the patient's infection.

The present invention provides DNA chips for detecting the multiple mutations in HIV genes associated with resistance to different therapeutics. These DNA chips allow physicians to monitor mutations over time and to change therapeutics if resistance develops. Some chips also provide probes for diagnosis of pathogenic microorganisms that typically occur in AIDS patients.

1. Selection of HIV reference sequence

The chips are designed to contain probes exhibiting complementarity to a particular reference sequence. The chips are used to read a target sequence comprising either the reference sequence itself or variants of that sequence. The sequence selected as a reference sequence can be from anywhere in the HIV genome, but should preferably cover a region of the HIV genome in which mutations associated with drug resistance are known to occur. A reference sequence is usually between about 5, 10, 20, 50, 100, 5000, 1000, 5,000 or 10,000 bases in length, and preferably is about 100–1700 bases in length. The reference sequence is usually selected so that it encompasses at least part of the reverse transcriptase sequence encoded by the pol gene. Preferably, the reference sequence encompasses all, or substantially all (i.e, about 75 or 90%) of the reverse transcriptase gene. Reverse transcriptase is the target of several drugs and as noted, above, the coding sequence is the site of many mutations associated with drug resistance. In some chips, the reference sequence contains the entire region coding reverse transcriptase (850 bp), and in other chips, subfragments thereof. In some chips, the reference sequence includes other subfragments of the pol gene encoding HIV protease or endonuclease, instead of, or as well as the segment encoding reverse transcriptase. In some chips, the reference sequence also includes other HIV genes such as env or gag as well as or instead of the reverse transcriptase gene. Certain regions of the gag and env genes are relatively well conserved, and their detection provides a means for identifying and quantifying the amount of HIV virus infecting a patient. In some chips, the reference sequence comprises an entire HIV genome.

It is not critical from which strain of HIV the reference sequence is obtained. HIV strains are classified as HIV-I or HIV-II, and within these generic groupings there are several strains and polymorphic variants of each of these. BRU, SF2, HXB2, HXB2R are examples of HIV-1 strains, the sequences of which are available from GenBank. The reverse transcriptase genes of the BRU and SF2 strains differ at 23 nucleotides. The HXB2 and HXB2R strains have the same reverse transcriptase gene sequence, which differs from that of the BRU strain at four nucleotides, and that of SF2 by 27 nucleotides. In some chips, the reference sequence corresponds exactly to the reverse transcriptase sequence in the wildtype version of a strain. In other chips, the reference sequence corresponds to a consensus sequence of several HIV strains. In some chips, the reference sequence corresponds to a mutant form of a HIV strain.

2. Chip Design

Chips are designed in accordance with the tiling strategy described in co-pending application U.S. Ser. No. 08/143, 312. There are advantages in some applications in using a minimal set of oligonucleotides specific to the sequence of interest, rather than a set of all possible N-mers. That is, a chip comprises an array of oligonucleotide probes, which are complementary to a reference sequence and immobilized to a support. The array is subdivided into at least four probe sets. Each probe set contains a series of overlapping probes, with one probe for each nucleotide of interest in the reference sequence. For each nucleotide in the reference sequence, the first probe set has a corresponding probe that is exactly complementary to subsequence of the reference sequence that includes that nucleotide. Thus, each probe in the first probe set is effectively paired with a particular nucleotide in the reference sequence, and either component of the pair can be described as corresponding to the other. As discussed infra, the identity of the nucleotide in the reference sequence (or a variant thereof) is read from the hybridization signal of the corresponding probe. The position in each probe occupied by the complement to the corresponding nucleotide is termed the integration position (also sometimes known as the position of substitution or position of mismatch). Usually, the first probe set has a probe corresponding to every nucleotide in the reference sequence. Occasionally certain positions in the reference sequence may be of little interest, and probes corresponding to those positions are not included. Conceptually, omission of certain probes in analysis of a full-length reference sequence is equivalent to analysis of a subsequence from the reference sequence using a full set of probes.

For each probe in the first set, there are three corresponding probes from three additional probe sets. Thus, the four sets of probes provide a total of four corresponding probes for each nucleotide in the reference sequence. Usually, the probes from the three additional probe sets are identical to the corresponding probe from the first probe set with one exception. The exception is that the interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Occasionally, the probes from the additional three probes are identical (with the exception of the interrogation position) to a contiguous subsequence of the corresponding probe from the first probe set, rather than to the full-length probe. In this case, the subsequence includes the interrogation position and is usually differs from the full-length probe in the omission of 1, 2, 3, 4, 5, 6, 7, 8, 9 or 10 nucleotides (depending on the length of the full-length probe).

Figure 1B:
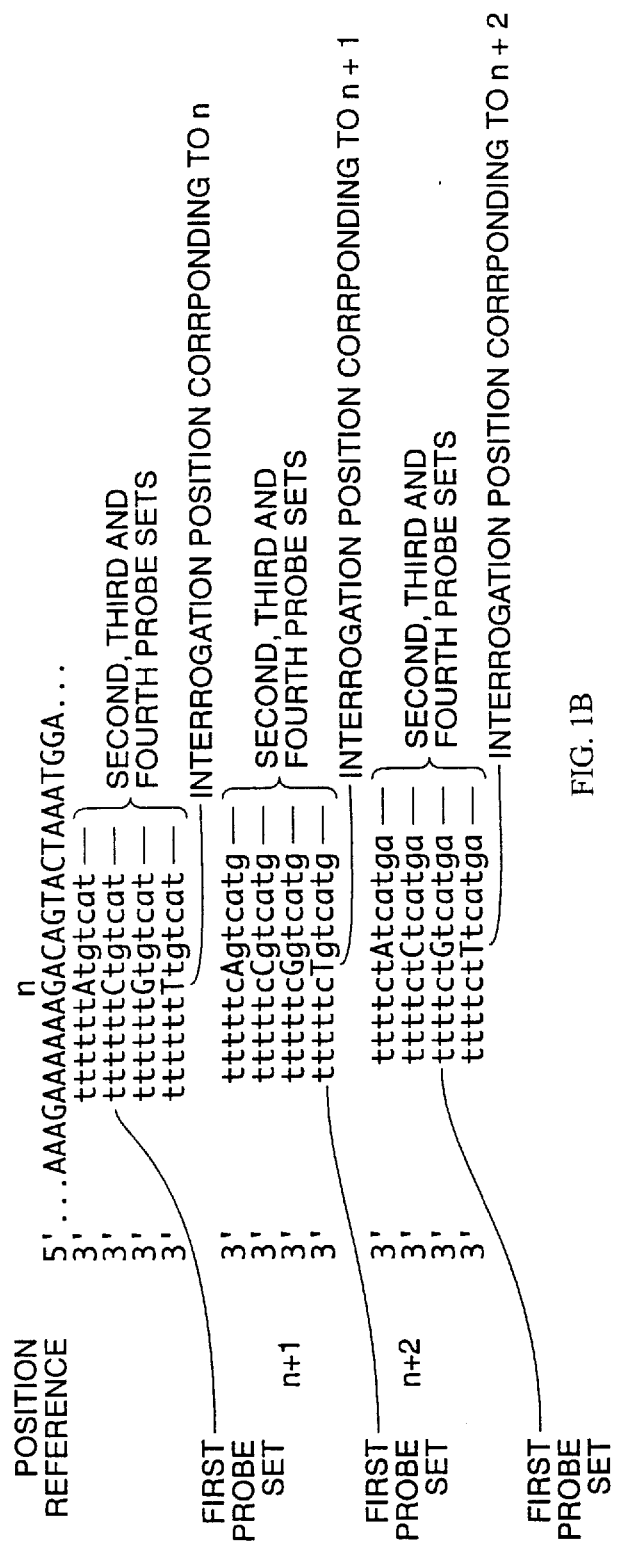

For conceptual simplicity, the probes in a set are usually arranged in order of the sequence in a lane across the chip. A lane contains a series of overlapping probes, which represent or tile across, the selected reference sequence (see FIG. 1). The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column. Each probe in a lane usually differs from its predecessor in the lane by the omission of a base at one end and the inclusion of additional base at the other end as shown in FIG. 1. However, this orderly progression of probes can be interrupted by the inclusion of control probes or omission of probes in certain columns of the array. Such columns serve as controls to orient the chip, or gauge the background of target sequence nonspecifically bound to the chip.

Figure 2:
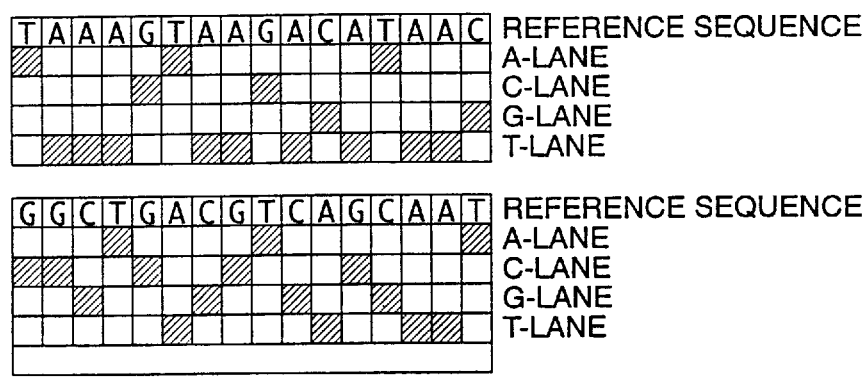
FIG. 2 (SEQ ID NOS. 28 through 33): An illustrative tiled array of the invention, in which probes are laid down in A-, C-, G- and T-lanes. The shading in the upper portion of the Figure shows the probe lane exhibiting perfect complementarity to the reference sequence for each nucleotide position in the reference sequence. When the chip is hybridized to the reference sequence, the shaded lanes show higher hybridization signals than the other lanes at the same position. The lower portion of the Figure shows the probes occupying the column marked by an arrow when the probes length is 15 and the interrogation position 7.

The probes sets are usually laid down in lanes such that all probes having an interrogation position occupied by an A form an A-lane, all probes having an interrogation position occupied by a C form a C-lane, all probes having an interrogation position occupied by a G form a G-lane, and all probes having an interrogation position occupied by a T (or U) form a T lane (or a U lane). See FIG. 2. The interrogation position on a column of probes corresponds to the position in the target sequence whose identity is determined from analysis of hybridization to the probes in that column. The interrogation position can be anywhere in a probe but is usually at or near the central position of the probe to maximize differential hybridization signals between a perfect match and a single-base mismatch. For example, for an 11 mer probe, the central position is the sixth nucleotide.

Although the array of probes is usually laid down in rows and columns as described above, such a physical arrangement of probes on the chip is not essential. Provided that the spatial location of each probe in an array is known, the data from the probes can be collected and processed to yield the sequence of a target irrespective of the physical arrangement of the probes on a chip. In processing the data, the hybridization signals from the respective probes can be reasserted into any conceptual array desired for subsequent data reduction whatever the physical arrangement of probes on the chip.

A range of lengths of probes can be employed in the chips (e.g., from about 9 mers to 21 mers). Usually, the probes have an odd number of bases, so that the interrogation position occurs in the exact center of the probe. In some chips, all probes are the same size. Some chips employ different groups of probe sets, in which the probes are of the same size within a group, but differ between different groups. For example, some chips have one group comprising a set of four probes as described above in which all the probes are 11 mers, together with a second group comprising a set of four probes in which all of the probes are 13 mers. Of course, additional groups of probes can be added. Thus, some chips contain, e.g., four groups of probes having sizes of 11 mers, 13 mers, 15 mers and 17 mers. Other chips have different size probes within the same group of four probe sets. In these chips, the probes in the first set can vary in length independently of each other. Probe in the other sets are usually the same length as the probe occupying the same column from the first set. However, occasionally different lengths of probes can be included at the same column position in the four lanes. The different length probes are included to equalize hybridization signals from probes irrespective whether A—T or C—G bonds are formed at the interrogation position.

The length of probe can be important in distinguishing between a perfectly matched probe and probes showing a single-base mismatch with the target sequence. The discrimination is usually greater for short probes. Shorter probes are usually also less susceptible to formation of secondary structures. However, the absolute amount of target sequence bound, and hence the signal, is greater for larger probes. The probe length representing the optimum compromise between these competing considerations may vary depending on inter alia the GC content of a particular region of the target DNA sequence. In some regions of the target, short probes (e.g., 11 mers) may provide information that is inaccessible from longer probes (e.g., 19 mers) and vice versa. Maximum sequence information can be read by including several groups of different sized probes on the chip as noted above. However, for many regions of the target sequence, such a strategy provides redundant information in that the same sequence is read multiple times from the different groups of probes. Equivalent information can be obtained from a single group of different sized probes in which the sizes are selected to optimize readable sequence at particular regions of the target sequence. The appropriate size of probes at different regions of the target sequence can be determined from, e.g., FIG. 5, which compares the readability of different sized probes in different regions of a target. The strategy of customizing probe length within a single group of probe sets minimizes the total number of probes required to read a particular target sequence. This leaves ample capacity for the chip to include probes to other reference sequences (e.g., 16S RNA for pathogenic microorganisms) as discussed below.

The probes are designed to be complementary to either the coding or noncoding strand of the HIV reference sequence. If only one strand is to be read, it is preferable to read the coding strand. The greater percentage of A residues in this strand relative to the noncoding strand generally result in fewer regions of ambiguous sequence. Some chips contain separate groups of probes, one complementary to the coding strand, the other complementary to the noncoding strand. Independent analysis of coding and noncoding strands provides largely redundant information. However, the regions of ambiguity in reading the coding strand are not always the same as those in reading the noncoding strand. Thus, combination of the information from coding and noncoding strands increases the overall accuracy of sequencing.

Some chips contain additional probes or groups of probes designed to be complementary to a second reference sequence. The second reference sequence is often a subsequence of the first reference sequence bearing one or more commonly occurring HIV mutations or interstrain variations (e.g., within codons 67, 70, 215 or 219 of the reverse transcriptase gene). The second group of probes is designed by the same principles as described above except that the probes exhibit complementarity to the second reference sequence. The inclusion of a second group is particular useful for analyzing short subsequences of the primary reference sequence in which multiple mutations are expected to occur within a short distance commensurate with the length of the probes (i.e., two mutations within 9 to 21 bases). Alternatively, the chips may contain additional probe(s) that do not form part of a tiled array as noted above, but rather serves as probe(s) for a conventional reverse dot blot. For example, the presence of mutation can be detected from binding of a target sequence to a single oligomeric probe harboring the mutation. Preferably, an additional probe containing the equivalent region of the wildtype sequence is included as a control.

The total number of probes on the chips depends on the length of the reference sequence and the options selected with respect to inclusion of multiple probe lengths and secondary groups of probes to provide confirmation of the existence of common mutations. To read much or all of the HIV reverse transcriptase gene (857 b for the BRU strain), chips typically contain at least 857×4=3428 thousand probes. However, it is entirely feasible and often desirable to construct chips containing much larger numbers of probes, for example, 16,000, 50,000, 100,000, $10^6$ or $10^7$ probes.

3. Preparation of target polynucleotide

The target HIV polynucleotide, whose sequence is to be determined, is usually isolated from blood samples (peripheral blood lymphocytes or PBMC) in the form of RNA. The RNA is reverse transcribed to DNA, and the DNA product is then amplified. Depending on the selection of primers and amplifying enzyme, the amplification product can be RNA or DNA.

When the target strand is prepared in single-stranded form as in preparation of target RNA, the sense of the strand should of course be complementary to that of the probes on the chip. This is achieved by appropriate selection of primers. primers for amplification of target are shown in the table below. The target is preferably fragmented before application to the chip to reduce or eliminate the formation of secondary structures in the target. The average size of targets segments following hybridization must, however, remain larger than the size of probe on the chip.

match to the target sequence whereas the others will usually exhibit at least a one base pair mismatch. The probe exhibiting a perfect match usually produces a substantially greater hybridization signal than the other three probes in the column and is thereby easily identified. However, in some regions of the target sequence, the distinction between a perfect match and a one-base mismatch is less clear. Thus, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read. A lower call ratio results in fewer ambiguous calls, but can result in more erroneous calls. It has been found that at a call ratio of 1.2 virtually all calls are accurate. However, a small but significant number of bases (e.g., up to about 10% of the reverse transcriptase sequence) have to be scored as ambiguous.

Figure 5A:
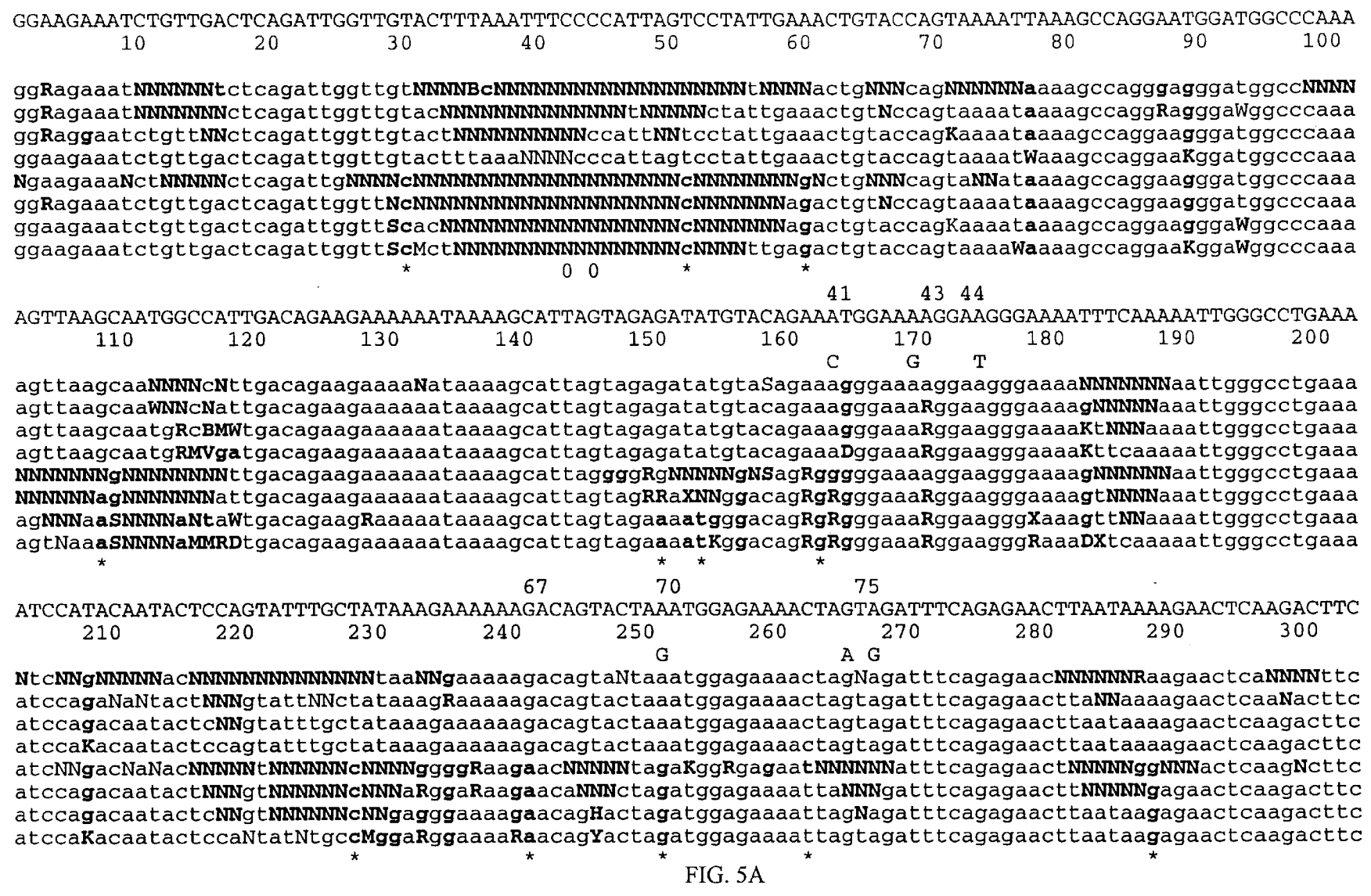
Figure 5B:
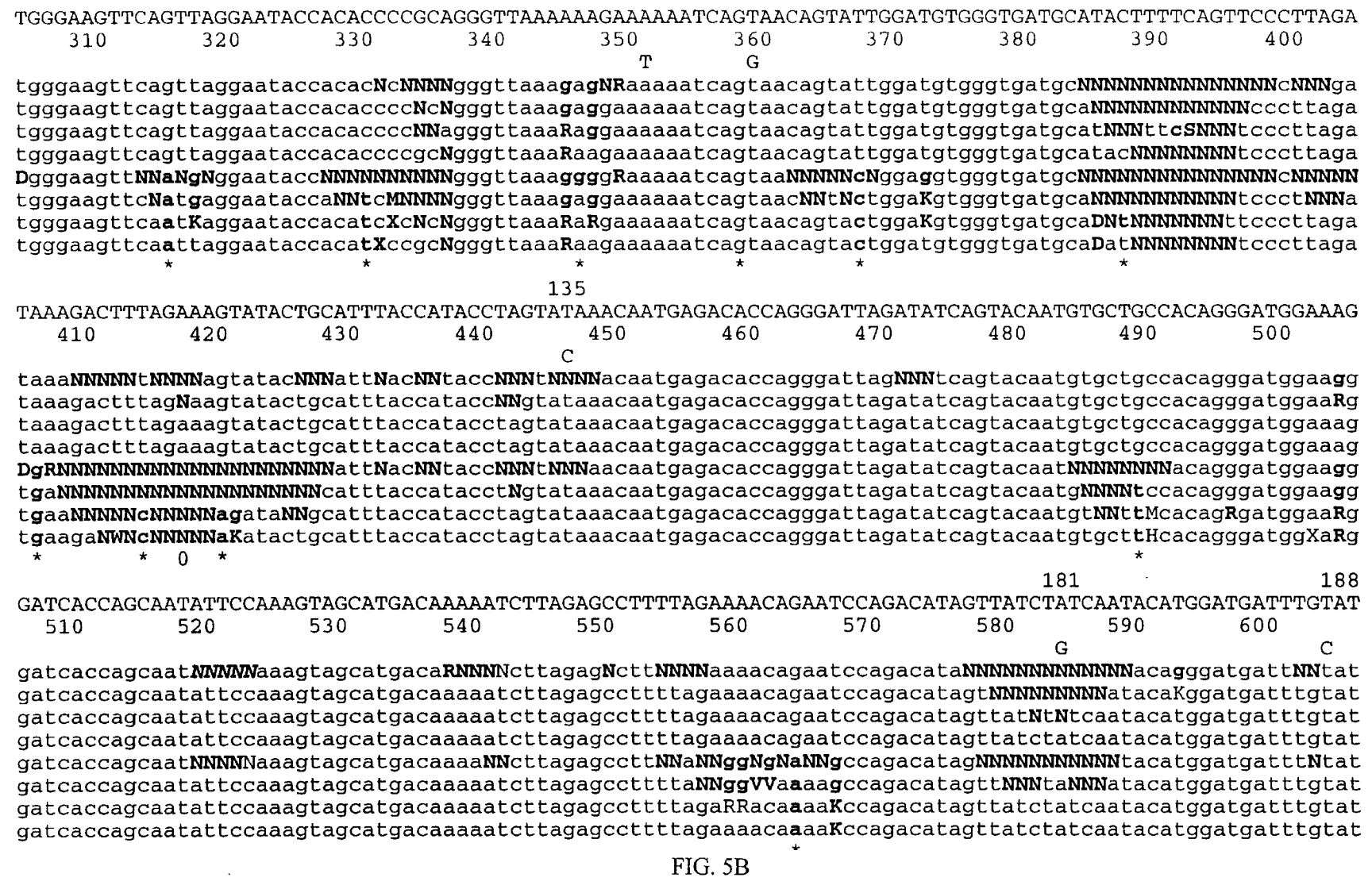
Figure 5C:
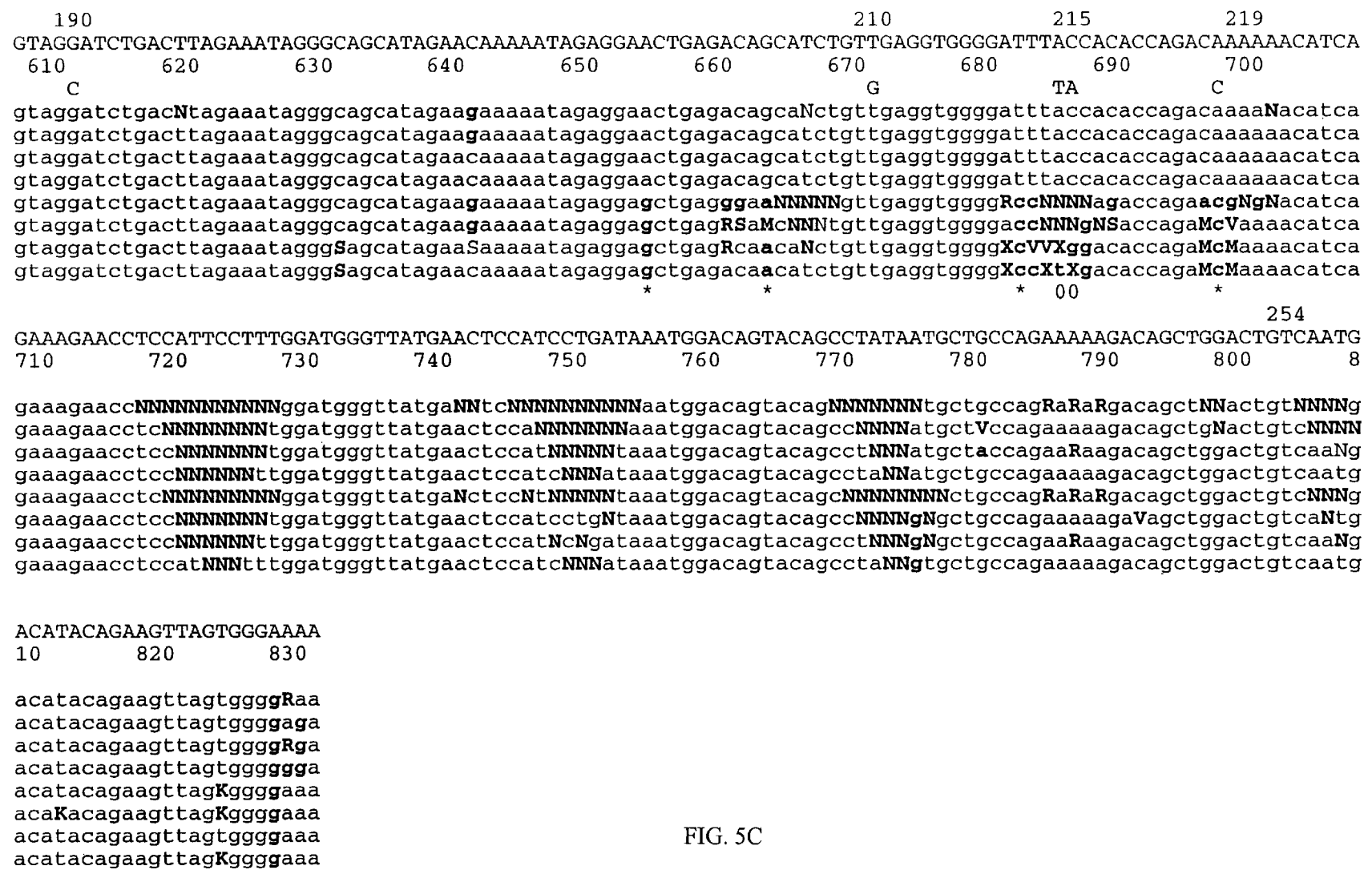

Although small regions of the target sequence can sometimes be ambiguous, these regions usually occur at the same or similar segments in different HIV variants. Thus, for each mutation known to be associated with acquisition of drug resistance, it is known in advance whether that mutation is likely to occur within a region of unambiguously determinable sequence. FIG. 5 shows that most of the commonly occurring mutations do occur in regions of the HV 273 reverse transcriptase sequence that can be read unambiguously. Thus, most of the commonly occurring mutations can be detected by a chip containing an array of probes based on a single reference sequence.

An array of probes is most useful for analyzing the HIV reference sequence from which the probes were designed and variants of that sequence exhibiting substantial sequence similarity with the reference sequence (e.g., single-base mutants). When an array is used to analyze the exact

TABLE 2

AMPLIFICATION OF TARGET

| TARGET SIZE | FORWARD PRIMER | REVERSE PRIMER |
|---|---|---|
| 1,742 bp | GTAGAATTCTGTTGACTCAGATTGG (SEQ ID NO:1) | GATAAGCTTGGGCCTTATCTATTCCAT (SEQ ID NO.7) |
| 535 bp | AAATCCATACAATACTCCAGTATTTGC (SEQ ID NO.2) | ACCCATCCAAAGGAATGGAGGTTCTTTC (SEQ ID NO.8) |
| 323 bp | Genbank #K02013 1889–1908 AATTAACCCTCACTAAAGGGAGA ggaagaatctgttgactcagattggt (RT#1-T3) (SEQ ID NO.3) AATTAACCCTCACTAAAGGGAga tcgacgcaggactcggcttgctgaa (SEQ ID NO.4) TAATACGACTCACTATAGGGAGA tcgacgcaggactcggcttgctgaa (SEQ ID NO.5) AATTAACCCTCACTAAAGGGAGA ccttgtaagtcattggtcttaaaggta (SEQ ID NO.6) | bases 2211–2192 CTTTAATACGACTCACTATAGGGAtttccccca ctaacttctgtatgtcattgaca-3'(89-391 T7) (SEQ ID NO.9) |

4. Analysis of Chip

The chips are read by comparing the fluorescence intensities of target bound to the probes at an array. Specifically, a comparison is performed between each lane of probes (e.g., A, C, G and T lanes) at each columnar position (physical or conceptual). For a particular columnar position, the lane showing the greatest hybridization signal is called as the nucleotide present at the position in the target sequence corresponding to the interrogation position in the probes. The corresponding position in the target sequence is that aligned with the interrogation position in the probes when the probes and target are maximally aligned. Of the four probes in a column, only one can exhibit a perfect reference sequence from which it was designed, one probe will exhibit a perfect match to the reference sequence, and the other three probes in the same column will exhibit single-base mismatches. Thus, discrimination between hybridization signals is high and accurate sequence is obtained. High accuracy is also obtained when an array is used for analyzing a target sequence comprising a variant of the reference sequence that has a single mutation relative to the reference sequence, or several widely spaced mutations relative to the reference sequence. At the mutant loci, one probe exhibits a perfect match to the target, and the other three probes occupying the same column exhibit single-base mismatches, the difference (with respect to analysis of the reference sequence) being the lane in which the perfect match occurs.

For HIV target sequences from a strain showing a high degree of divergence from the reference strain or for HIV variants incorporating several closely spaced mutations from the reference strain, a single group of probes (i.e., designed with respect to a single reference sequence) will not always provide accurate sequence for the highly variant region of this sequence. At some particular columnar positions, it may be that no single probe exhibits perfect complementarity to the target and that any comparison must be based on different degrees of mismatch between the four probes. Such a comparison does not always allow the target nucleotide corresponding to that columnar position to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read.

The presence of short regions of difficult-to-read target because of closely spaced mutations, insertions or deletion, does not prevent determination of the remaining sequence of the target as different regions of a target sequence are determined independently. Moreover, such ambiguities as might result from analysis of diverse variants with a single group of probes can be avoided by including multiple groups of probe sets on a chip. For example, one group of probes can be designed based on a full-length reference sequence, and the other groups on subsequences of the reference sequence incorporating frequently occurring mutations. Further groups of probes can be designed based on reference sequences from different strains of HIV.

A particular advantage of the present sequencing strategy over conventional sequencing methods is the capacity simultaneously to detect multiple strains or variants of HIV. Frequently, patients are infected with different proportions of many strains or variants of HIV. The presence of multiple strains or variants of HIV is detected from the relative signals of the four probes at the array columns corresponding to the target nucleotides at which diversity occurs. The relative signals at the four probes for the mixture under test are compared with the corresponding signals from a homogeneous reference sequence. An increase in a signal from a probe that is mismatched with respect to the reference sequence, and a corresponding decrease in the signal from the probe which is matched with the reference sequence signal the presence of a mutant strain in the mixture. The extent in shift in hybridization signals of the probes is related to the proportion of mutant strain in the mixture. Shifts in relative hybridization signals can be quantitatively related to proportions of reference and mutant sequence by prior calibration of the chip with seeded mixtures of the mutant and reference sequences. By this means, a chip can be used to detect variant or mutant strains constituting as little as 5, 20, or 25% of a mixture of stains. Similar principles allow the simultaneous analysis of multiple strains of HIV even when none is identical to the reference sequence. For example, with a mixture of two mutant strains bearing first and second mutations, there would be a variation in the hybridization patterns of probes having interrogation positions corresponding to the first and second mutations relative to the hybridization pattern with the reference sequence. At each position, one of the probes having a mismatched interrogation position relative to the reference sequence would show an increase in hybridization signal, and the probe having a matched interrogation position relative to the reference sequence would show a decrease in hybridization signal. Analysis of the hybridization pattern of the mixture of mutant strains, preferably in comparison with the hybridization pattern to the reference sequence, indicates the presence of two strains, the position and nature of the mutation in each strain, and the relative proportions of each strain.

In a variation of the above method, the different components in a mixture of HIV target sequences are differentially labelled before being applied to the array. For example, a variety of fluorescent labels emitting at different wavelength are available. The use of differential labels allows independent analysis of different targets bound simultaneously to the array.

5. Detection of Microorganisms Commonly Found in AIDS Patients

In another aspect of the invention, chips are provided for simultaneous detection of HIV and microorganisms that commonly parasitize AIDS patients (e.g., cytomegalovirus (CMV), *Pneumocystis carini* (PCP), fungi, mycobacteria, candida albicans). Non-HIV viral pathogens are detected and their drug resistance determined using a similar strategy as for HIV. That is groups of probes are designed to show complementarity to a target sequence from a region of the genome of a nonviral pathogen known to be associated with acquisition of drug resistance. For example, CMV and HSV viruses, which frequently co-parasitize AIDS patients, undergo mutations to acquire resistance to acyclovir.

For detection of non-viral pathogens, the chips include an array of probes which allow full-sequence determination of 16S ribosomal RNA or corresponding genomic DNA of the pathogens. The additional probes are designed by the same principles as described above except that the target sequence is a variable region from a 16S RNA (or corresponding DNA) of a pathogenic microorganism. Alternatively, the target sequence can be a consensus sequences of variable 16S rRNA regions from multiple organisms. 16S ribosomal DNA and RNA is present in all organisms (except viruses) and the sequence of the DNA or RNA is closely related to the evolutionary genetic distance between any two species. Hence, organisms which are quite close in type (e.g., all mycobacteria) share a common region of 16S rDNA, and differ in other regions (variable regions) of the 16S rRNA. These differences can be exploited to allow identification of the different subtype strains. The full sequence of 16S ribosomal RNA or DNA read from the chip is compared against a database of the sequence of thousands of known pathogens to type unambiguously type most nonviral pathogens infecting AIDS patients.

In a further embodiment, the invention provides chips which also contain probes for detection of bacterial genes conferring antibiotic resistance. An antibiotic gene can be detected by hybridization to a single probe employed in a reverse dot blot format. Alternatively, a group of probes can be designed according to the same principles discussed above to read all or part the DNA sequence encoding an antibiotic resistance gene. Analogous probes groups are designed for reading other antibiotic resistance gene sequences. Antibiotic resistance frequently resides in one of the following genes in microorganisms coparasitizing AIDS patients: rpoB (encoding RNA polymerase), katG (encoding catalase peroxidase, and DNA gyrase A and B genes.

The inclusion of probes for combinations of tests on a single chip simulates the clinical diagnosis tree that a physician would follow based on the presentation of a given syndrome which could be caused by any number of possible pathogens. Such chips allow identification of the presence and titer of HIV in a patient, identification of the HIV strain type and drug resistance, identification of opportunistic pathogens, and identification of the drug resistance of such pathogens. Thus, the physician is simultaneously apprised of the full spectrum of pathogens infecting the patient and the most effective treatments therefor.

7. Exemplary HIV Chips (a) HV 273

The HV 273 chip contains an array of oligonucleotide probes for analysis of an 857 base HIV amplicon between nucleotides 2090 and 2946 (HIVBRU strain numbering). The chip contains four groups of probes: 11 mers, 13 mers, 15 mers and 17 mers. From top to bottom, the HV 273 chip is occupied by rows of 11 mers, followed by rows of 13 mers, followed by rows of 15 mers followed by rows of 17 mers. The interrogation position is nucleotide 6, 7, 8 and 9 respectively in the different sized chips. This arrangement of the different sized probes is referred to as being "in series." Within each size group, there are four probe sets laid down in an A-lane, a C-lane a G-lane and a T-lane respectively. Each lane contains an overlapping series of probes with one probe for each nucleotide in the 2090–2946 HIV reverse transcriptase reference sequence. (i.e., 857 probes per lane). The lanes also include a few column positions which are empty or occupied by control probes. These positions serve to orient the chip, determine background fluorescence and punctuate different subsequences within the target. The chip has an area of 1.28×1.28 cm, within which the probes form a 130×135 matrix (17,550 cells total). The area occupied by each probe (i.e., a probe cell) is about 98×95 microns.

The chip was tested for its capacity to sequence a reverse transcriptase fragment from the HIV strain SF2. An 831 bp RNA fragment (designated pPol19) spanning most of the HIV reverse transcriptase coding sequence was amplified by PCR, using primers tagged with T3 and T7 promoter sequences. The primers, designated RT#l-T3 and 89–391 T7 are shown in Table 2; see also Gingeras et al., *J. Inf. Dis.* 164, 1066–1074 (1991) (incorporated by reference in its entirety for all purposes). RNA was labelled by incorporation of fluorescent nucleotides. The RNA was fragmented by heating and hybridized to the chip for 40 min at 30 degrees. Hybridization signals were quantified by fluorescence imaging.

Taking the best data from the four probes sets at each position in the target sequence, 715 out of 821 bases were read correctly (87%). (Comparisons are based on the sequence of pPol19 determined by the conventional dideoxy method to be identical to SF2). In general, the longer sized probes yielded more sequence than the shorter probes. Of the 21 positions at which the SF2 and BRU strains diverged within the target, 19 were read correctly.

Many of the short ambiguous regions in the target arise in segments of the target flanking the points at which the SF2 and BRU sequences diverge. These ambiguities arise because in these regions the comparison of hybridization signals is not drawn between perfectly matched and single base mismatch probes but between a single-mismatched probe and three probes having two mismatches. These ambiguities in reading an SF2 sequence would not detract from the chip's ability to read a BRU sequence either alone or in a mixture with an SF2 target sequence.

In a variation of the above procedure, the chip was treated with RNase after hybridization of the pPol19 target to the probes. Addition of RNase digests mismatched target and thereby increases the signal to noise ratio. RNase treatment increased the number of correctly read bases to 743/821 or 90% (combining the data from the four groups of probes).

In a further variation, the RNA target was replaced with a DNA target containing the same segment of the HIV genome. The DNA probe was prepared by linear amplification using Taq polymerase, RT#1-T3 primer, and fluorescein d-UTP label. The DNA probe was fragmented with uracil DNA glycosylase and heat treatment. The hybridization pattern across the array and percentage of readable sequence were similar to those obtained using an RNA target. However, there were a few regions of sequence that could be read from the RNA target that could not be read from the DNA target and vice versa.

(b) HV 407 Chip

Figure 3A:
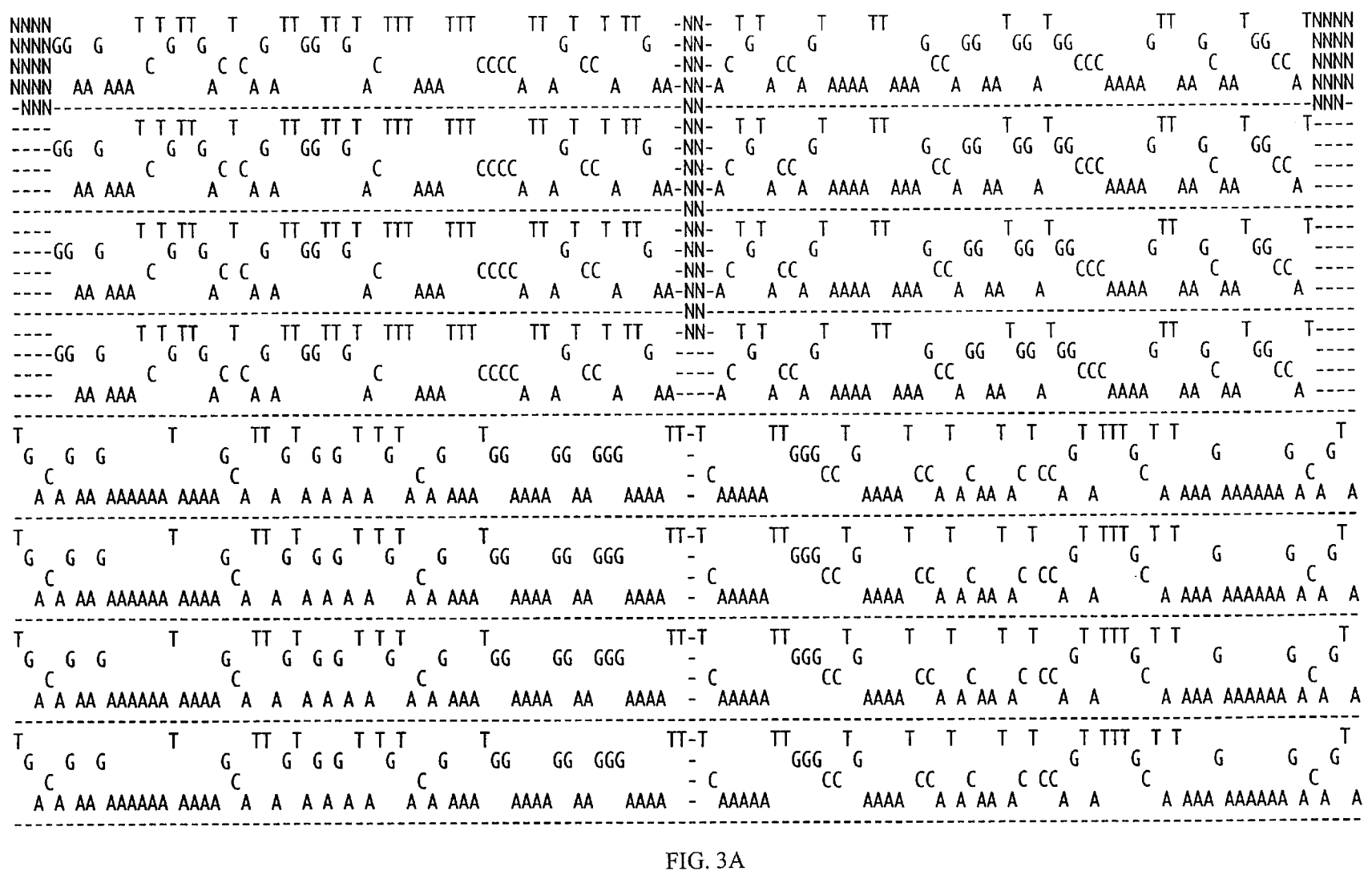
Figure 3B:
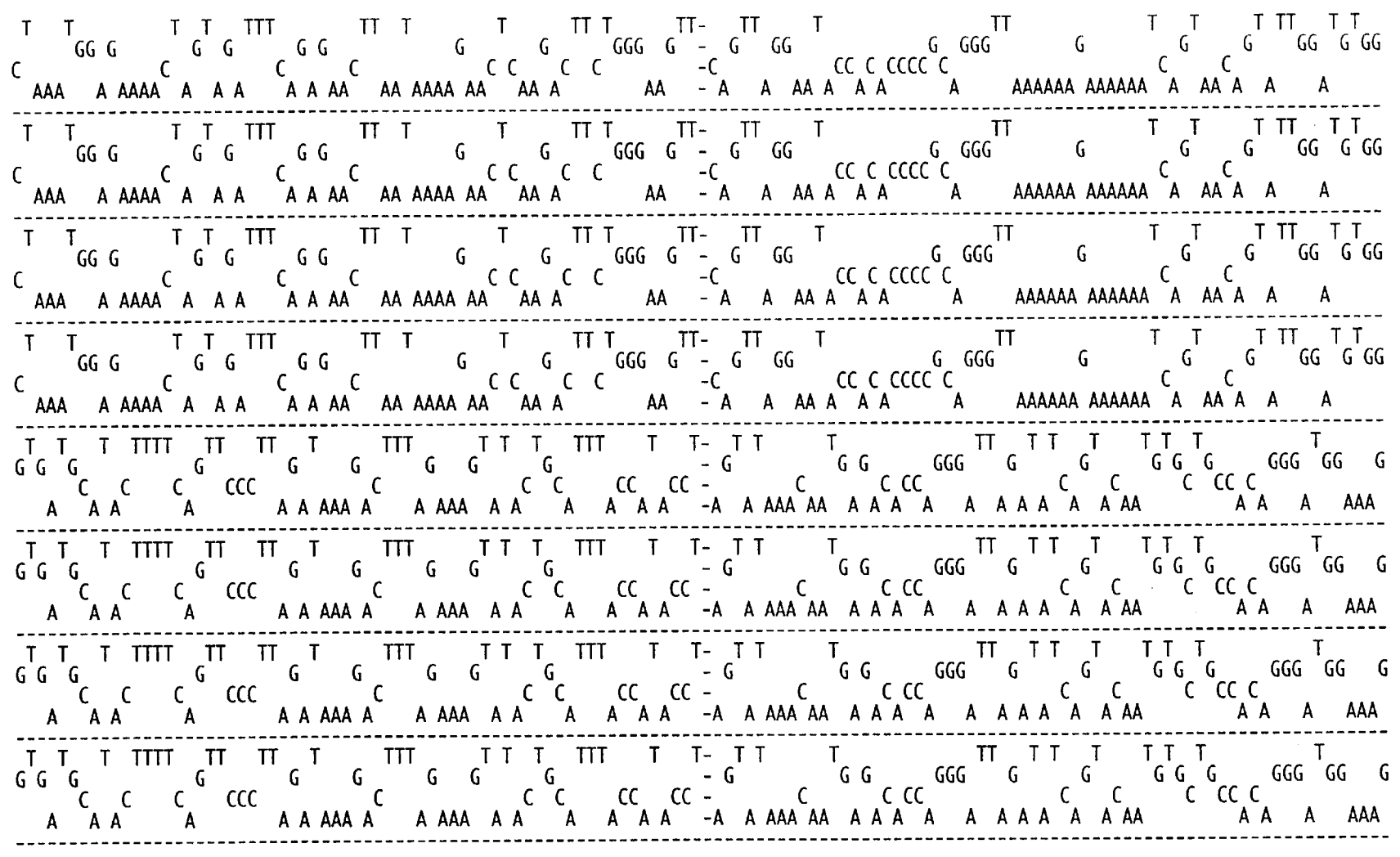
Figure 3C:
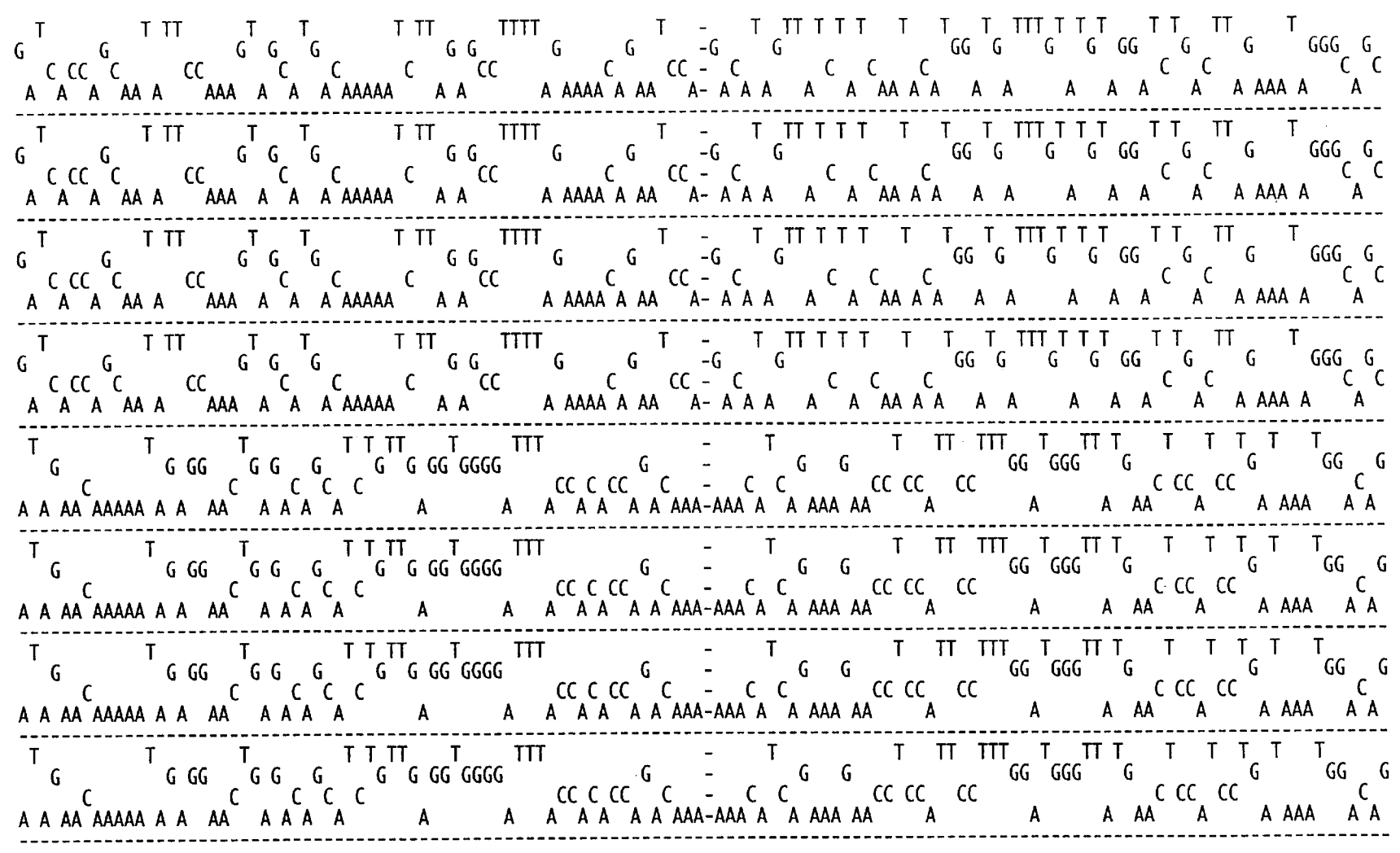
Figure 3D:
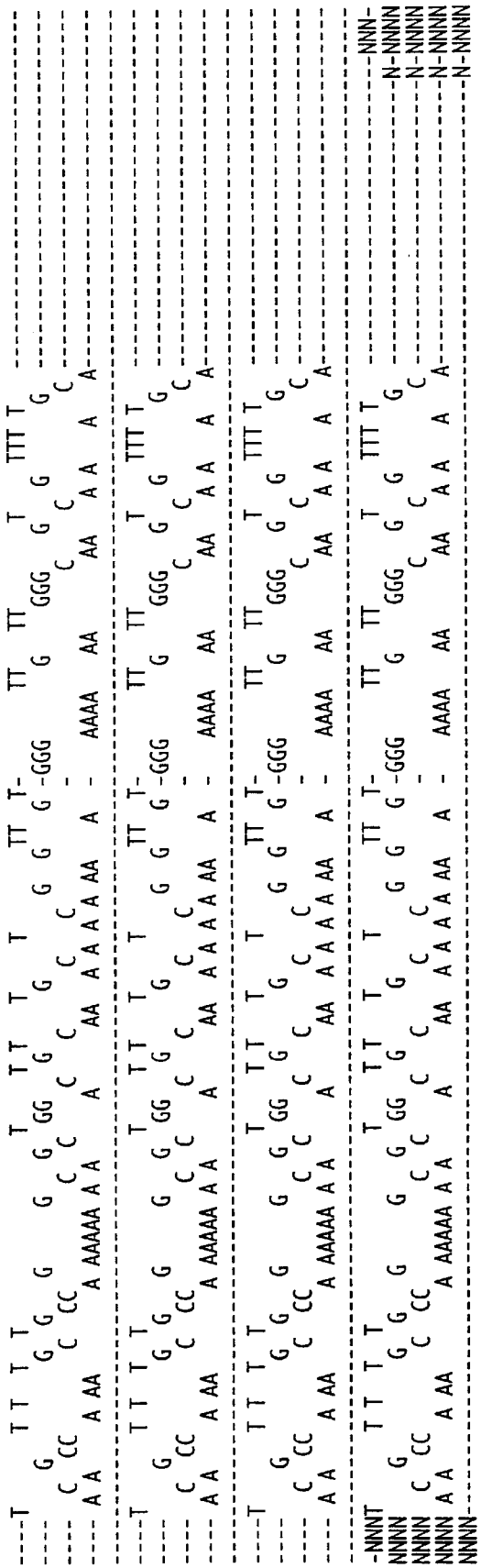
FIG. 3: Layout of probes on the HV 407 chip. The Figure shows successive rows of sequence each of which is subdivided into four lanes. The four lanes correspond to the A-, C-, G- and T-lanes on the chip. Each probe is represented by the nucleotide occupying its interrogation position. The letter "N" indicates a control probe or empty column. The different sized-probes are laid out in parallel. That is, from top-to-bottom, a row of 13 mers is followed by a row of 15 mers, which is followed by a row of 17 mers, which is followed by a row of 19 mers.

The 407 chip was designed according to the same principles as the HV 273 chip, but differs in several respects. First, the oligonucleotide probes on this chip are designed to exhibit perfect sequence identity (with the exception of mismatch position on each probe) to the HIV strain SF2 (rather than the BRU strain as was the case for the HV 273 chip). Second, the 407 chip contains 13 mers, 15 mers, 17 mers and 19 mers (with interrogation positions at nucleotide 7, 8, 9 and 10 respectively), rather than the 11 mers, 13 mers, 15 mers and 17 mers on the HV 273 chip. Third, the different sized groups of oligomers are arranged in parallel in place of the in-series arrangement on the HV 273 chip. In the parallel arrangement, the chip contains from top to bottom a row of 13 mers, a row of 15 mers, a row of 17 mers, a row of 19 mers, followed by a further row of 13 mers, a row of 15 mers, a row of 17 mers, a row of 19 mers, followed by a row of 15 mers, and so forth. Each row contains 4 lanes of probes, an A lane, a C lane, a G lane and a T lane, as described above. The probes in each lane tile across the reference sequence. The layout of probes on the HV 407 chip is shown in FIG. 3.

Figure 4:
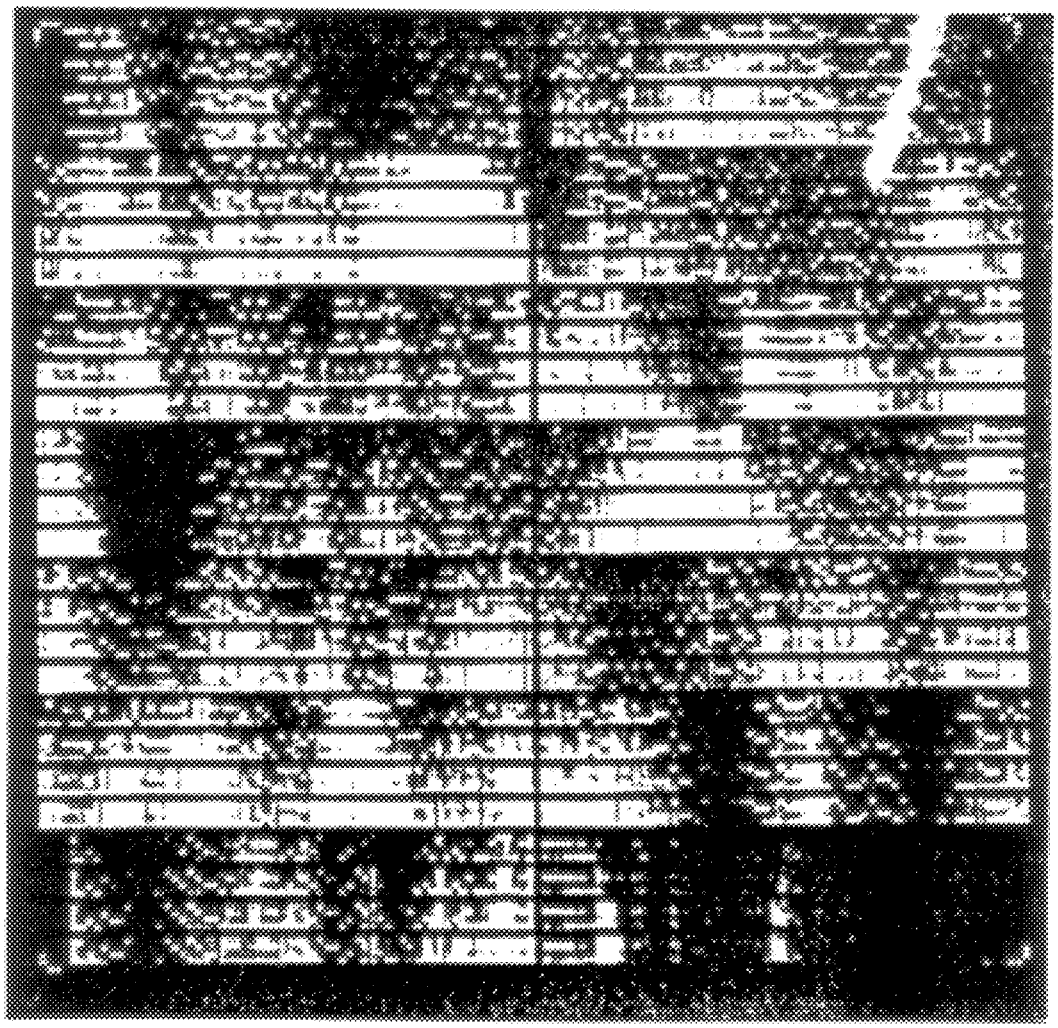
FIG. 4: Fluorescence pattern of HV 407 hybridized to a target sequence (pPol19) identical to the chips reference sequence.

The 407 chip was separately tested for its ability to sequence two targets, pPol19 RNA and HXB2 RNA. pPol19 contains an 831 bp fragment from the SF2 reverse transcriptase gene which exhibits perfect complementarity to the probes on the 407 chip (except of course for the interrogation positions in three of the probes in each column). HXB2 differs from the reference sequence at twenty-six positions within the target, including four positions in codons 67, 70, 215 and 219 associated with acquisition of drug resistance. Target RNA was prepared, labelled and fragmented as described above and hybridized to the HV 407 chip. The hybridization pattern for the pPol19 target is shown in FIG. 4.

The sequences read off the chip for the pPol19 and HXB2 targets are both shown in FIG. 5 (although the two sequences were determined in different experiments). The sequence labelled wildtype in the Figure is the reference sequence. The four lanes of sequence immediately below the reference sequence are the respective sequences read from the four-sized groups of probes for the pPol19 target (from top-to-bottom, 13 mers, 15 mers, 17 mers and 19 mers). The next four lanes of sequence are the sequences read from the four-sized groups of probes for the HXB2 target (from top-to-bottom in the same order). The regions of sequences shown in normal type are those that could be read unambiguously from the chip. Regions where sequence could not be accurately read are shown highlighted. Some regions of sequence that could not be read from one sized set of probes could be read from another. Taking the best result from the four sized groups of probes at each column position, about 97% of bases in the pPol19 sequence and about 90% of bases in the HXB2 sequence were read accurately. Of the twenty-six nucleotide differences between HXB2 and the reference sequence, twenty-four were read correctly including three of the nucleotide changes associated with acquisition of drug resistance. Of the ambiguous regions in the HXB2 sequence determination, most occurred in the HBX2 segments flanking points of divergence between the HBX2 and reference sequences. Notably, most of the common mutations in HIV reverse transcriptase associated with drug resistance (see Table 1) occur at sequence positions that can be read from the chip.

Figure 7:
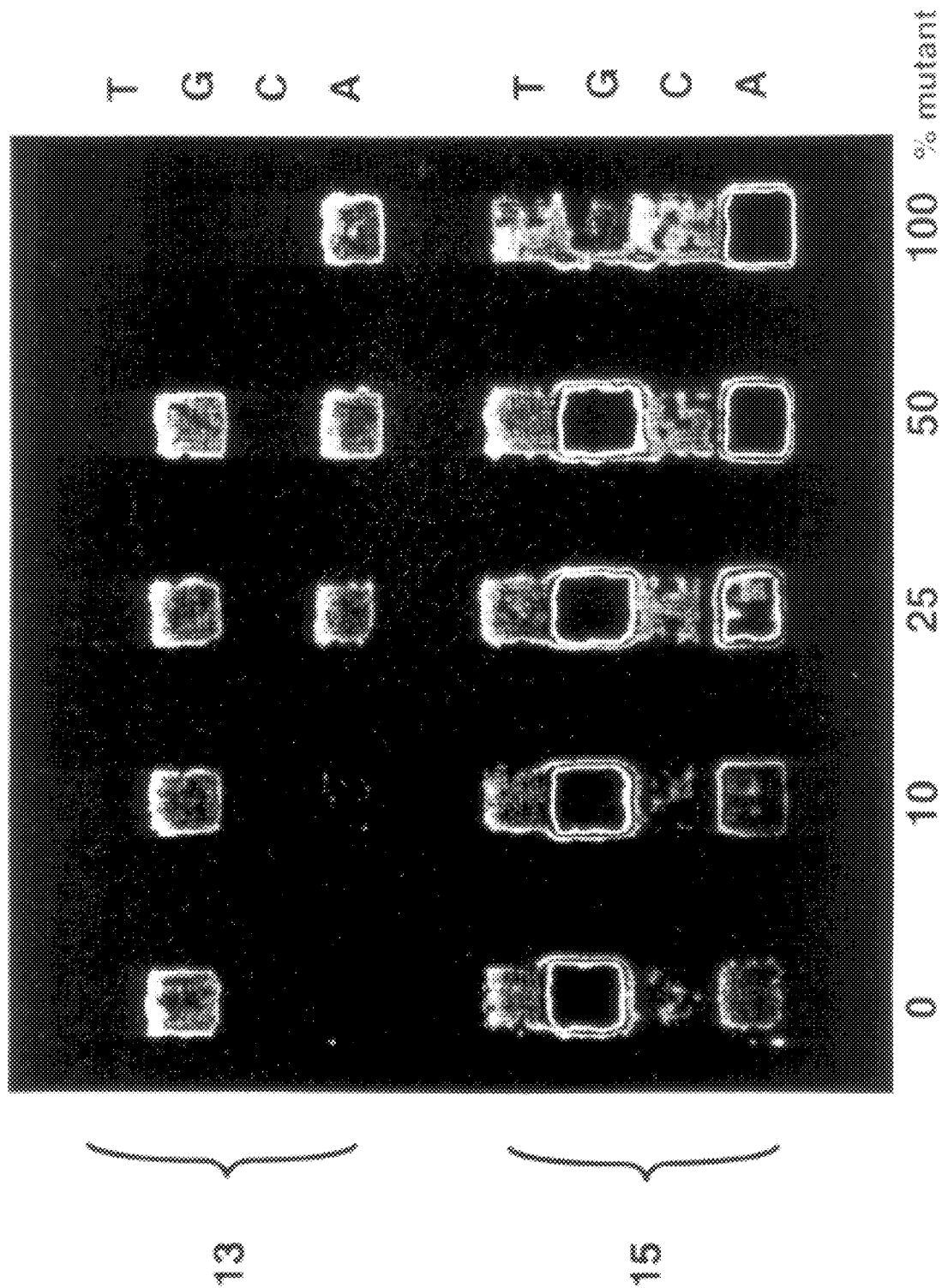
FIG. 7: Fluorescence intensities of target bound to 13 mers and 15 mers for different proportions of mutant and wildtype target. The fluorescence intensities are from probes having interrogation positions for reading the nucleotide at which the mutant and wildtype targets diverge.

The HV 407 chip has also been tested for its capacity to detect mixtures of different HIV strains. The mixture comprises varying proportions of two target sequences; one a segment of a reverse transcriptase gene from a wildtype SF2 strain, the other a corresponding segment from an SF2 strain bearing a codon 67 mutation. See FIG. 6. The Figure also represents the probes on the chip having an interrogation position for reading the nucleotide in which the mutation occurs. A single probe in the Figure represents four probes on the chip with the symbol (o) indicating the interrogation position, which differs in each of the four probes. FIG. 7 shows the fluorescence intensity for the four 13 mers and the four 15 mers having an interrogation position for reading the nucleotide in the target sequence in which the mutation occurs. As the percentage of mutant target is increase, the fluorescence intensity of the probe exhibiting perfect complementarity to the wildtype target decreases, and the intensity of the probe exhibiting perfect complementarity to the mutant sequence increases. The intensities of the other two probes do not change appreciably. It is concluded that the chip can be used to analyze simultaneously a mixture of strains, and that a strain comprising as little as ten percent of a mixture can be easily detected.

MODES OF PRACTICING THE INVENTION

A. VLSIPS™ Technology

Figure 8:
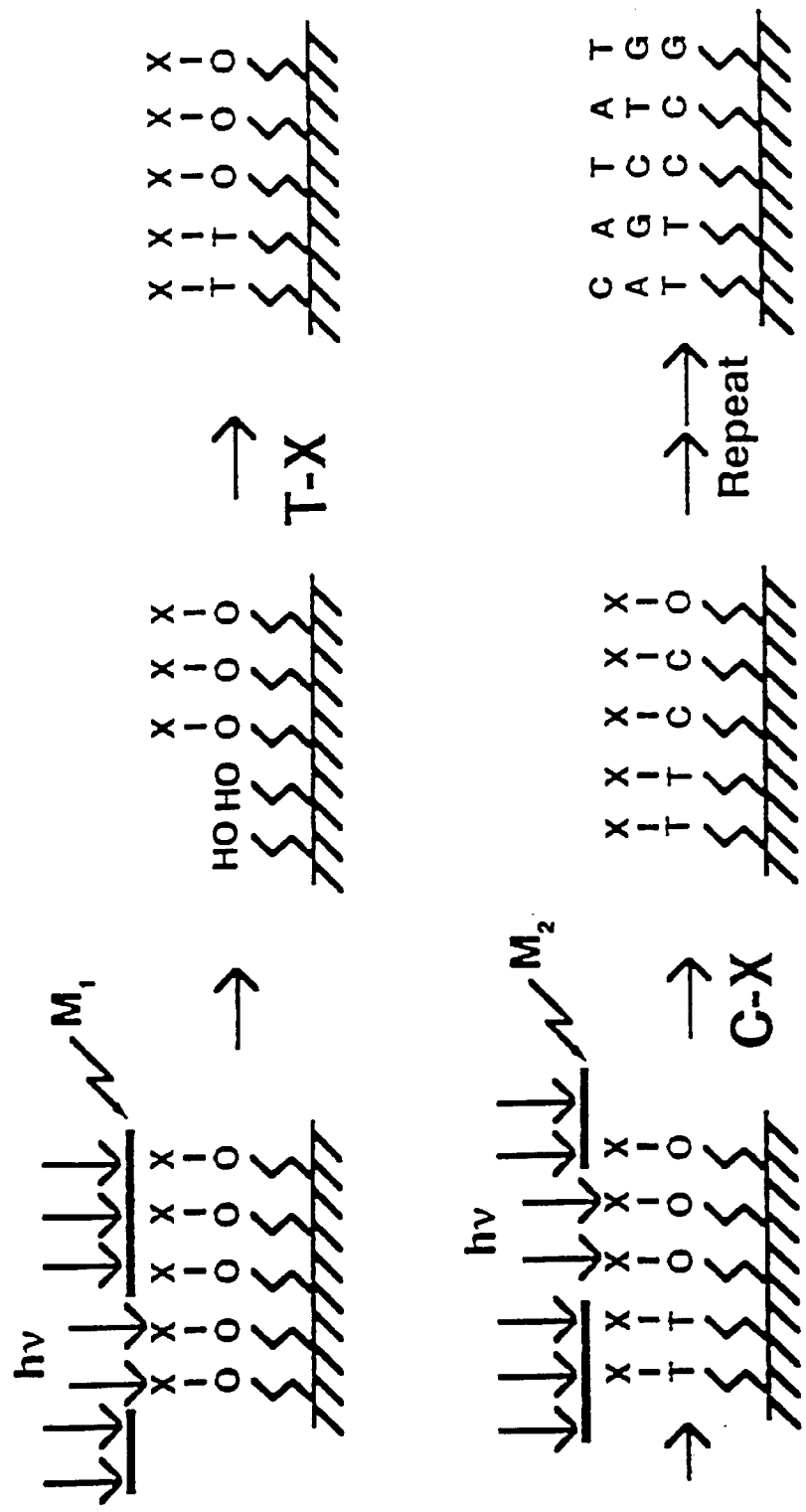
FIG. 8: VLSIPS™ technology applied to the light directed synthesis of oligonucleotides. Light (hv) is shone through a mask (M₁) to activate functional groups (—OH) on a surface by removal of a protecting group (X). Nucleoside building blocks protected with photoremovable protecting groups (T—X, C—X) are coupled to the activated areas. By repeating the irradiation and coupling steps, very complex arrays of oligonucleotides can be prepared.
Figure 9:
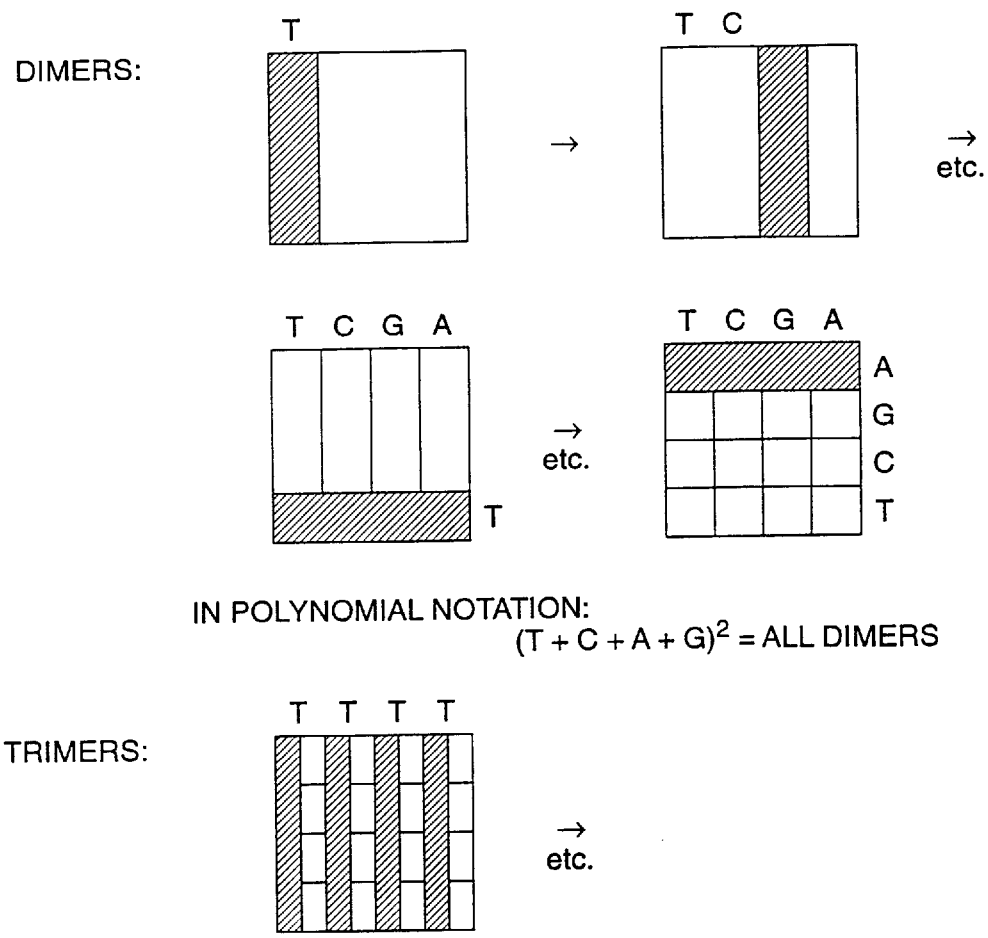
FIG. 9: Use of the VLSIPS™ process to prepare "nucleoside combinatorials" or oligonucleotides synthesized by coupling all four nucleosides to form dimers, trimers, and so forth.

As noted above, the VLSIPS™ technology is described in a number of patent publications and is preferred for making the oligonucleotide arrays of the invention. For completeness, a brief description of how this technology can be used to make and screen DNA chips is provided in this Example and the accompanying Figures. In the VLSIPS method, light is shone through a mask to activate functional (for oligonucleotides, typically an —OH) groups protected with a photoremovable protecting group on a surface of a solid support. After light activation, a nucleoside building block, itself protected with a photoremovable protecting group (at the 5'—OH), is coupled to the activated areas of the support. The process can be repeated, using different masks or mask orientations and building blocks, to prepare very dense arrays of many different oligonucleotide probes. The process is illustrated in FIG. 8; FIG. 9 illustrates how the process can be used to prepare "nucleoside combinatorials" or oligonucleotides synthesized by coupling all four nucleosides to form dimers, trimers and so forth.

New methods for the combinatorial chemical synthesis of peptide, polycarbamate, and oligonucleotide arrays have recently been reported (see Fodor et al., 1991, *Science* 251: 767–773; Cho et al., 1993, *Science* 261: 1303–1305; and Southern et al., 1992, *Genomics* 13: 1008–10017, each of which is incorporated herein by reference). These arrays, or biological chips (see Fodor et al., 1993, *Nature* 364: 555–556, incorporated herein by reference), harbor specific chemical compounds at precise locations in a high-density, information rich format, and are a powerful tool for the study of biological recognition processes. A particularly exciting application of the array technology is in the field of DNA sequence analysis. The hybridization pattern of a DNA target to an array of shorter oligonucleotide probes is used to gain primary structure information of the DNA target. This format has important applications in sequencing by hybridization, DNA diagnostics and in elucidating the thermodynamic parameters affecting nucleic acid recognition.

Conventional DNA sequencing technology is a laborious procedure requiring electrophoretic size separation of labeled DNA fragments. An alternative approach, termed Sequencing By Hybridization (SBH), has been proposed (Lysov et al., 1988, *Dokl. Akad. Nauk SSSR* 303:1508–1511; Bains et al., 1988, *J. Theor. Biol.* 135:303–307; and Drmanac et al., 1989, *Genomics* 4:114–128, incorporated herein by reference). This method uses a set of short oligonucleotide probes of defined sequence to search for complementary sequences on a longer target strand of DNA. The hybridization pattern is used to reconstruct the target DNA sequence. It is envisioned that hybridization analysis of large numbers of probes can be used to sequence long stretches of DNA. In immediate applications of this hybridization methodology, a small number of probes can be used to interrogate local DNA sequence.

The strategy of SBH can be illustrated by the following example. A 12-mer target DNA sequence, AGCCTAGCT-GAA (SEQ ID NO. 10), is mixed with a complete set of octanucleotide probes. If only perfect complementarity is considered, five of the 65,536 octamer probes —TCGGATCG, CGGATCGA, GGATCGAC, GATCGACT, and ATCGACTT will hybridize to the target. Alignment of the overlapping sequences from the hybridizing probes reconstructs the complement of the original 12-mer target:

TCGGATCG
CGGATCGA
GGATCGAC
GATCGACT
TCGGATTCGACTT (SEQ ID NO.11)

Hybridization methodology can be carried out by attaching target DNA to a surface. The target is interrogated with a set of oligonucleotide probes, one at a time (see Strezoska et al., 1991, *Proc. Natl. Acad. Sci. USA* 88:10089–10093, and Drmanac et al., 1993, *Science* 260:1649–1652, each of which is incorporated herein by reference). This approach can be implemented with well established methods of immobilization and hybridization detection, but involves a large number of manipulations. For example, to probe a sequence utilizing a full set of octanucleotides, tens of thousands of hybridization reactions must be performed. Alternatively, SBH can be carried out by attaching probes to a surface in an array format where the identity of the probes at each site is known. The target DNA is then added to the array of probes. The hybridization pattern determined in a single experiment directly reveals the identity of all complementary probes.

As noted above, a preferred method of oligonucleotide probe array synthesis involves the use of light to direct the synthesis of oligonucleotide probes in high-density, miniaturized arrays. Photolabile 5'-protected N-acyl-deoxynucleoside phosphoramidites, surface linker chemistry, and versatile combinatorial synthesis strategies have been developed for this technology. Matrices of spatially-defined oligonucleotide probes have been generated, and the ability to use these arrays to identify complementary sequences has been demonstrated by hybridizing fluorescent labeled oligonucleotides to the DNA chips produced by the methods. The hybridization pattern demonstrates a high degree of base specificity and reveals the sequence of oligonucleotide targets.

The basic strategy for light-directed oligonucleotide synthesis (1) is outlined in FIG. 8. The surface of a solid support modified with photolabile protecting groups (X) is illuminated through a photolithographic mask, yielding reactive hydroxyl groups in the illuminated regions. A 3'—O-phosphoramidite activated deoxynucleoside (protected at the 5'-hydroxyl with a photolabile group) is then presented to the surface and coupling occurs at sites that were exposed to light. Following capping, and oxidation, the substrate is rinsed and the surface illuminated through a second mask, to expose additional hydroxyl groups for coupling. A second 5'-protected, 3'—O-phosphoramidite activated deoxynucleoside is presented to the surface. The selective photo-deprotection and coupling cycles are repeated until the desired set of products is obtained.

Light directed chemical synthesis lends itself to highly efficient synthesis strategies which will generate a maximum number of compounds in a minimum number of chemical steps. For example, the complete set of $4^n$ polynucleotides (length n), or any subset of this set can be produced in only 4xn chemical steps. See FIG. 9. The patterns of illumination and the order of chemical reactants ultimately define the products and their locations. Because photolithography is used, the process can be miniaturized to generate high-density arrays of oligonucleotide probes. For an example of the nomenclature useful for describing such arrays, an array containing all possible octanucleotides of dA and dT is written as $(A+T)^8$. Expansion of this polynomial reveals the identity of all 256 octanucleotide probes from AAAAAAAA to TTTTTTTT. A DNA array composed of complete sets of dinucleotides is referred to as having a complexity of 2. The array given by (A+T+C+G)8 is the full 65,536 octanucleotide array of complexity four.

To carry out hybridization of DNA targets to the probe arrays, the arrays are mounted in a thermostatically controlled hybridization chamber. Fluorescein labeled DNA targets are injected into the chamber and hybridization is allowed to proceed for ½ to 2 hours. The surface of the matrix is scanned in an epifluorescence microscope (Zeiss Axioscop 20) equipped with photon counting electronics using 50–100 $\mu$W of 488 nm excitation from an Argon ion laser (Spectra Physics model 2020). All measurements are acquired with the target solution in contact with the probe matrix. Photon counts are stored and image files are presented after conversion to an eight bit image format. See FIG. 13.

When hybridizing a DNA target to an oligonucleotide array, N=Lt–(Lp–1) complementary hybrids are expected, where N is the number of hybrids, Lt is the length of the DNA target, and Lp is the length of the oligonucleotide probes on the array. For example, for an 11-xist hybridized to an octanucleotide array, N=4. Hybridizations with mismatches at positions that are 2 to 3 residues from either end of the probes will generate detectable signals. Modifying the above expression for N, one arrives at a relationship estimating the number of detectable hybridizations (Nd) for a DNA target of length Lt and an array of complexity C. Assuming an average of 5 positions giving signals above background:

$$Nd=(1+5(C-1))[Lt-(Lp-1)].$$

Arrays of oligonucleotides can be efficiently generated by light-directed synthesis and can be used to determine the identity of DNA target sequences. Because combinatorial strategies are used, the number of compounds increases exponentially while the number of chemical coupling cycles increases only linearly. For example, expanding the synthesis to the complete set of $4^8$ (65,536) octanucleotides will add only four hours to the synthesis for the 16 additional cycles. Furthermore, combinatorial synthesis strategies can be implemented to generate arrays of any desired composition. For example, because the entire set of dodecamers ($4^{12}$) can be produced in 48 photolysis and coupling cycles ($b^n$ compounds requires bxn cycles), any subset of the dodecamers (including any subset of shorter oligonucleotides) can be constructed with the correct lithographic mask design in 48 or fewer chemical coupling steps. In addition, the number of compounds in an array is limited only by the density of synthesis sites and the overall array size. Recent experiments have demonstrated hybridization to probes synthesized in 25 $\mu$m sites. At this resolution, the entire set of 65,536 octanucleotides can be placed in an array measuring 0.64 cm square, and the set of 1,048,576 dodecanucleotides requires only a 2.56 cm array.

Genome sequencing projects will ultimately be limited by DNA sequencing technologies. Current sequencing methodologies are highly reliant on complex procedures and require substantial manual effort. Sequencing by hybridization has the potential for transforming many of the manual efforts into more efficient and automated formats. Light-directed synthesis is an efficient means for large scale production of miniaturized arrays for SBH. The oligonucleotide arrays are not limited to primary sequencing applications. Because single base changes cause multiple changes in the hybridization pattern, the oligonucleotide arrays provide a powerful means to check the accuracy of previously elucidated DNA sequence, or to scan for changes within a sequence. In the case of octanucleotides, a single base change in the target DNA results in the loss of eight complements, and generates eight new complements. Matching of hybridization patterns may be useful in resolving sequencing ambiguities from standard gel techniques, or for rapidly detecting DNA mutational events. The potentially very high information content of light-directed oligonucleotide arrays will change genetic diagnostic testing. Sequence comparisons of hundreds to thousands of different genes will be assayed simultaneously instead of the current one, or few at a time format. Custom arrays can also be constructed to contain genetic markers for the rapid identification of a wide variety of pathogenic organisms.

Oligonucleotide arrays can also be applied to study the sequence specificity of RNA or protein-DNA interactions. Experiments can be designed to elucidate specificity rules of non Watson-Crick oligonucleotide structures or to investigate the use of novel synthetic nucleoside analogs for antisense or triple helix applications. Suitably protected RNA monomers may be employed for RNA synthesis. The oligonucleotide arrays should find broad application deducing the thermodynamic and kinetic rules governing formation and stability of oligonucleotide complexes.

Figure 10:
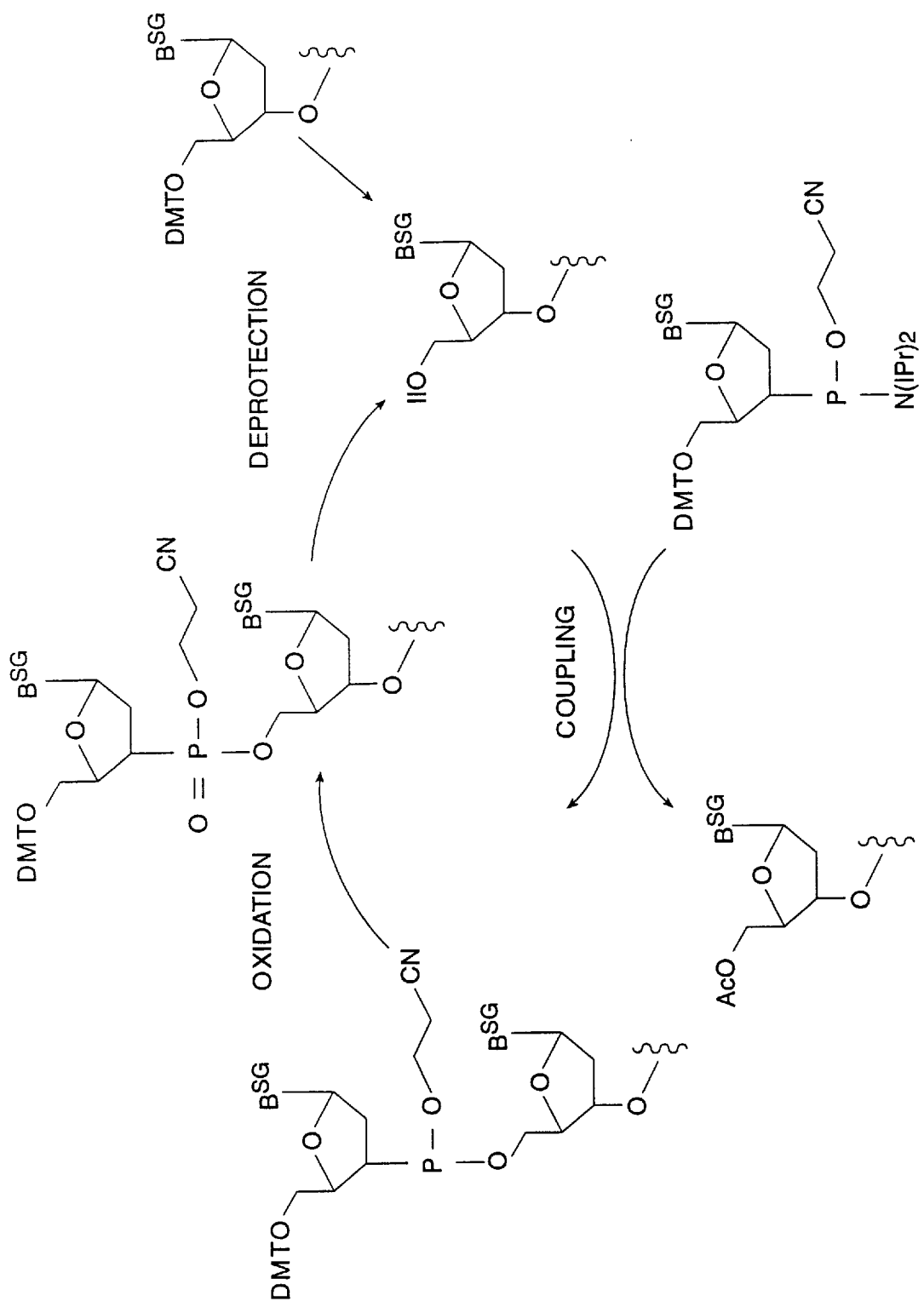
FIG. 10: Deprotection, coupling, and oxidation steps of a solid phase DNA synthesis method.
Figure 11:
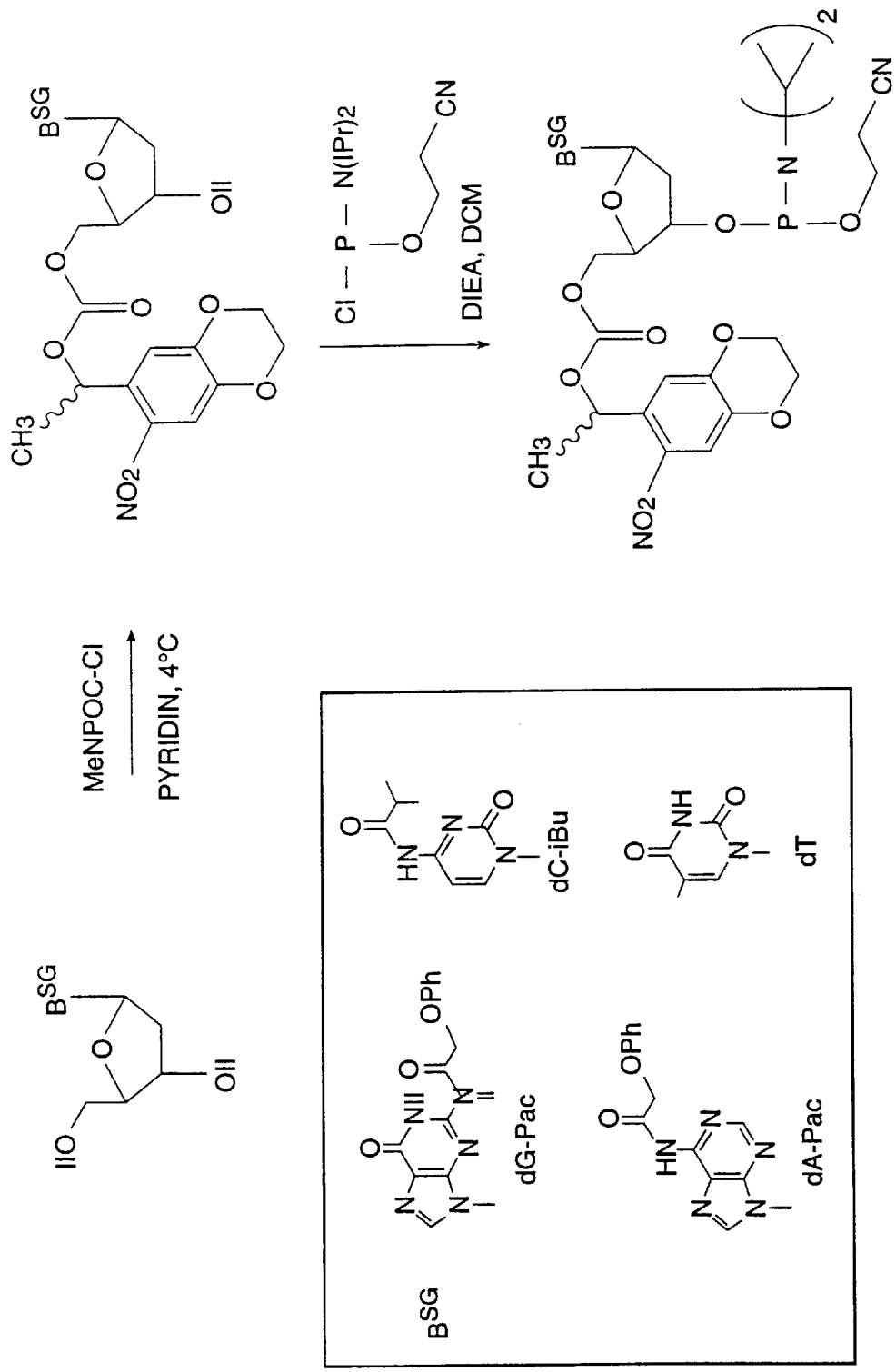
FIG. 11: An illustrative synthesis route for the nucleoside building blocks used in the VLSIPS™ method.
Figure 12:
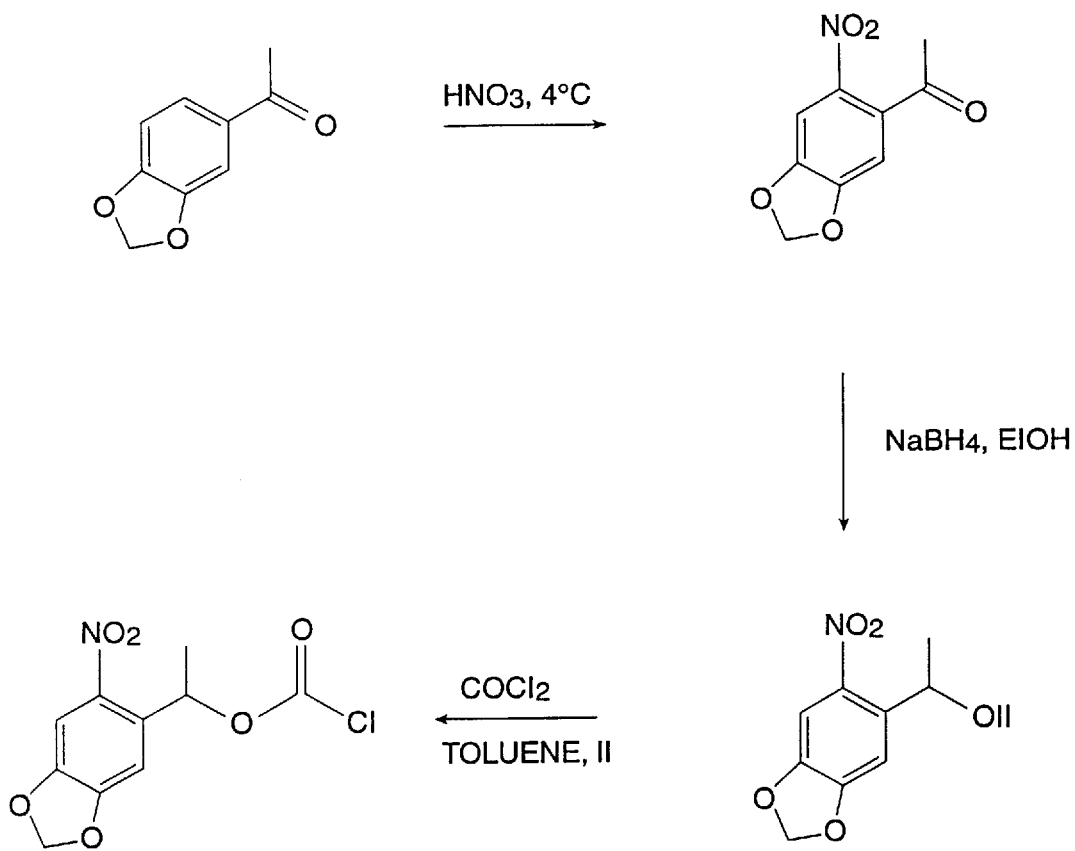
FIG. 12: A preferred photoremovable protecting group, MeNPOC, and preparation of the group in active form.

Other than the use of photoremovable protecting groups, the nucleoside coupling chemistry is very similar to that used routinely today for oligonucleotide synthesis. FIG. 10 shows the deprotection, coupling, and oxidation steps of a solid phase DNA synthesis method. FIG. 11 shows an illustrative synthesis route for the nucleoside building blocks used in the method. FIG. 12 shows a preferred photoremovable protecting group, MeNPOC, and how to prepare the group in active form. The procedures described below show how to prepare these reagents. The nucleoside building blocks are 5'-MeNPOC-THYMIDINE-3'-OCEP; 5'-MeNPOC-N⁴-t-BUTYL PHENOXYACETYL-DEOXYCYTIDINE-3'-OCEP; 5'-MeNPOC-N⁴-t-BUTYL PHENOXYACETYL-DEOXYGUANOSINE-3'-OCEP; and 5'-MeNPOC-N⁴-t-BUTYL PHENOXYACETYL-DEOXYADENOSINE-3'-OCEP.

1. Preparation of 4,5-methylenedioxy-2-nitroacetophenone

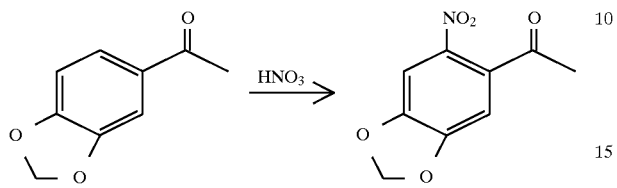

A solution of 50 g (0.305 mole) 3,4-methylenedioxyacetophenone (Aldrich) in 200 mL glacial acetic acid was added dropwise over 30 minutes to 700 mL of cold (2°–4° C.) 70% HNO₃ with stirring (NOTE: the reaction will overheat without external cooling from an ice bath, which can be dangerous and lead to side products). At temperatures below 0° C., however, the reaction can be sluggish. A temperature of 3°–5° C. seems to be optimal). The mixture was left stirring for another 60 minutes at 3°–5° C., and then allowed to approach ambient temperature. Analysis by TLC (25% EtOAc in hexane) indicated complete conversion of the starting material within 1–2 hr. When the reaction was complete, the mixture was poured into ~3 liters of crushed ice, and the resulting yellow solid was filtered off, washed with water and then suction-dried. Yield ~53 g (84%), used without further purification.

2. Preparation of 1-(4,5-Methylenedioxy-2-nitrophenyl) ethanol

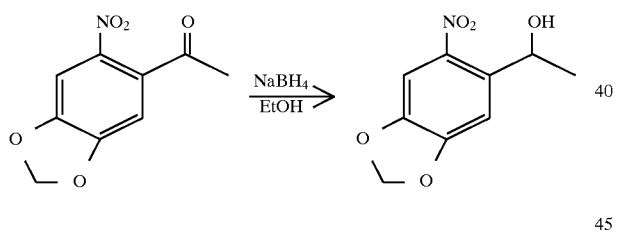

Sodium borohydride (10 g; 0.27 mol) was added slowly to a cold, stirring suspension of 53 g (0.25 mol) of 4,5-methylenedioxy-2-nitroacetophenone in 400 mL methanol. The temperature was kept below 10° C. by slow addition of the NaBH₄ and external cooling with an ice bath. Stirring was continued at ambient temperature for another two hours, at which time TLC (CH₂Cl₂) indicated complete conversion of the ketone. The mixture was poured into one liter of ice-water and the resulting suspension was neutralized with ammonium chloride and then extracted three times with 400 mL CH₂Cl₂ or EtOAc (the product can be collected by filtration and washed at this point, but it is somewhat soluble in water and this results in a yield of only ~60%). The combined organic extracts were washed with brine, then dried with MgSO₄ and evaporated. The crude product was purified from the main byproduct by dissolving it in a minimum volume of CH₂Cl₂ or THF(~175 ml) and then precipitating it by slowly adding hexane (1000 ml) while stirring (yield 51 g; 80% overall). It can also be recrystallized (eg., toluene-hexane), but this reduces the yield.

3. Preparation of 1-(4,5-methylenedioxy-2-nitrophenyl) ethyl chloroformate (MeNPOC-Cl)

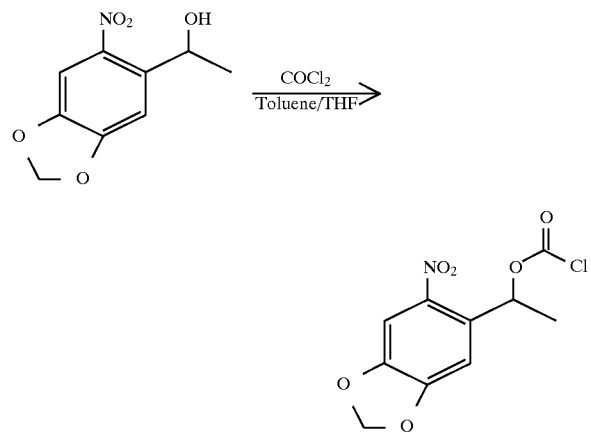

Phosgene (500 mL of 20% w/v in toluene from Fluka: 965 mmole; 4 eq.) was added slowly to a cold, stirring solution of 50 g (237 mmole; 1 eq.) of 1-(4,5-methylenedioxy-2-nitrophenyl) ethanol in 400 mL dry THF. The solution was stirred overnight at ambient temperature at which point TLC (20% Et₂O/hexane) indicated >95% conversion. The mixture was evaporated (an oil-less pump with downstream aqueous NaOH trap is recommended to remove the excess phosgene) to afford a viscous brown oil. Purification was effected by flash chromatography on a short (9×13 cm) column of silica gel eluted with 20% Et₂O/hexane. Typically 55 g (85%) of the solid yellow MeNPOC-Cl is obtained by this procedure. The crude material has also been recrystallized in 2–3 crops from 1:1 ether/hexane. On this scale, ~100 ml is used for the first crop, with a few percent THF added to aid dissolution, and then cooling overnight at −20° C. (this procedure has not been optimized). The product should be stored dessicated at −20° C.

4. Synthesis of 5'- Menpoc-2'-deoxynucleoside-3'-(N,N-diisopropyl 2-cyanoethyl phosphoramidites
(a.) 5'-MeNPOC-Nucleosides

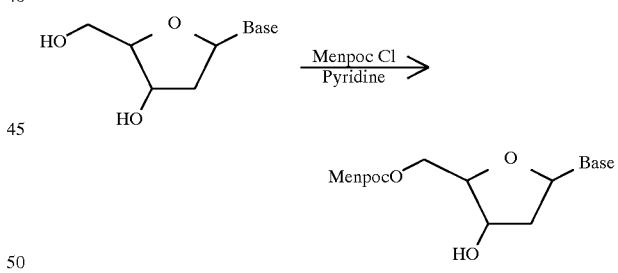

Base=THYMIDINE (T) ; N-4-ISOBUTYRYL 2'-DEOXYCYTIDINE (ibu-dC); N-2-PHENOXYACETYL 2'DEOXYGUANOSINE (PAC-dG); and N-6-PHENOXYACETYL 2'DEOXYADENOSINE (PAC-dA)

All four of the 5'-MeNPOC nucleosides were prepared from the base-protected 2¹-deoxynucleosides by the following procedure. The protected 2'-deoxynucleoside (90 mmole) was dried by co-evaporating twice with 250 mL anhydrous pyridine. The nucleoside was then dissolved in 300 mL anhydrous pyridine (or 1:1 pyridine/DMF, for the dG$^{PAC}$ nucleoside) under argon and cooled to ~2° C. in an ice bath. A solution of 24.6 g (90 mmole) MeNPOC-Cl in 100 mL dry THF was then added with stirring over 30 minutes. The ice bath was removed, and the solution allowed to stir overnight at room temperature (TLC: 5–10% MeOH in CH₂Cl₂; two diastereomers). After evaporating the solvents under vacuum, the crude material was taken up in 250 mL ethyl acetate and extracted with saturated aqueous $NaHCO_3$ and brine. The organic phase was then dried over $Na_2SO_4$, filtered and evaporated to obtain a yellow foam. The crude products were finally purified by flash chromatography (9×30 cm silica gel column eluted with a stepped gradient of 2%–6% MeOH in $CH_2Cl_2$). Yields of the purified diastereomeric mixtures are in the range of 65–75%.

(b.) 5'- Menpoc-2'-deoxynucleoside-3'-(N,N-diisopropyl 2-cyanoethyl phosphoramidites)

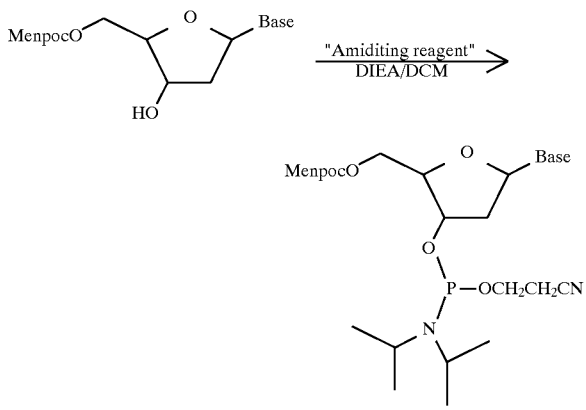

The four deoxynucleosides were phosphitylated using either 2-cyanoethyl-N,N-diisopropyl chlorophosphoramidite, or 2-cyanoethyl-N,N,N',N'-tetraisopropylphosphorodiamidite. The following is a typical procedure. Add 16.6 g (17.4 ml; 55 mmole) of 2-cyanoethyl-N,N,N',N'-tetraisopropylphosphorodiamidite to a solution of 50 mmole 5'-MeNPOC-nucleoside and 4.3 g (25 mmole) diisopropylammonium tetrazolide in 250 mL dry $CH_2Cl_2$ under argon at ambient temperature. Continue stirring for 4–16 hours (reaction monitored by TLC: 45:45:10 hexane/$CH_2Cl_2$/$Et_3N$). Wash the organic phase with saturated aqueous $NaHCO_3$ and brine, then dry over $Na_2SO_4$, and evaporate to dryness. Purify the crude amidite by flash chromatography (9×25 cm silica gel column eluted with hexane/$CH_2Cl_2$/TEA—45:45:10 for A, C, T; or 0:90:10 for G). The yield of purified amidite is about 90%.

B. Preparation of Labeled DNA/Hybridization to Array

1. PCR

PCR amplification reactions are typically conducted in a mixture composed of, per reaction: 1 μl genomic DNA; 10 μl each primer (10 pmol/μl stocks); 10 μl 10×PCR buffer (100 mM Tris.Cl pH8.5, 500 mM KCl, 15 mM $MgCl_2$); 10 μl 2 mM dNTPs (made from 100 mM dNTP stocks); 2.5 U Taq polymerase (Perkin Elmer AmpliTaq™, 5 U/μl); and $H_2O$ to 100 μl. The cycling conditions are usually 40 cycles (94° C. 45 sec, 55° C. 30 sec, 72° C. 60 sec) but may need to be varied considerably from sample type to sample type. These conditions are for 0.2 mL thin wall tubes in a Perkin Elmer 9600 thermocycler. See Perkin Elmer 1992/93 catalogue for 9600 cycle time information. Target, primer length and sequence composition, among other factors, may also affect parameters.

For products in the 200 to 1000 bp size range, check 2 μl of the reaction on a 1.5% 0.5×TBE agarose gel using an appropriate size standard (phiX174 cut with HaeIII is convenient). The PCR reaction should yield several picomoles of product. It is helpful to include a negative control (i.e., 1 μl TE instead of genomic DNA) to check for possible contamination. To avoid contamination, keep PCR products from previous experiments away from later reactions, using filter tips as appropriate. Using a set of working solutions and storing master solutions separately is helpful, so long as one does not contaminate the master stock solutions.

For simple amplifications of short fragments from genomic DNA it is, in general, unnecessary to optimize $Mg^{2+}$ concentrations. A good procedure is the following: make a master mix minus enzyme; dispense the genomic DNA samples to individual tubes or reaction wells; add enzyme to the master mix; and mix and dispense the master solution to each well, using a new filter tip each time.

2. Purification

Removal of unincorporated nucleotides and primers from PCR samples can be accomplished using the Promega Magic PCR Preps DNA purification kit. One can purify the whole sample, following the instructions supplied with the kit (proceed from section IIIB, 'Sample preparation for direct purification from PCR reactions'). After elution of the PCR product in 50 μl of TE or $H_2O$, one centrifuges the eluate for 20 sec at 12,000 rpm in a microfuge and carefully transfers 45 μl to a new microfuge tube, avoiding any visible pellet. Resin is sometimes carried over during the elution step. This transfer prevents accidental contamination of the linear amplification reaction with 'Magic PCR' resin. Other methods, e.g., size exclusion chromatography, may also be used.

3. Linear amplification

In a 0.2 mL thin-wall PCR tube mix: 4 μl purified PCR product; 2 μl primer (10 pmol/μl); 4 μl 10×PCR buffer; 4 μl dNTPs (2 mM dA, dC, dG, 0.1 mM dT); 4 μl 0.1 mM dUTP; 1 μl 1 mM fluorescein dUTP (Amersham RPN 2121); 1 U Taq polymerase (Perkin Elmer, 5 U/μl); and add H2O to 40 μl. Conduct 40 cycles (92° C. 30 sec, 55° C. 30 sec, 72° C. 90 sec) of PCR. These conditions have been used to amplify a 300 nucleotide mitochondrial DNA fragment but are generally applicable. Even in the absence of a visible product band on an agarose gel, there should still be enough product to give an easily detectable hybridization signal. If one is not treating the DNA with uracil DNA glycosylase (see Section 4), dUTP can be omitted from the reaction.

4. Fragmentation

Purify the linear amplification product using the Promega Magic PCR Preps DNA purification kit, as per Section 2 above. In a 0.2 mL thin-wall PCR tube mix: 40 μl purified labeled DNA; 4 μl 10×PCR buffer; and 0.5 μl uracil DNA glycosylase (BRL 1U/μl). Incubate the mixture 15 min at 37° C., then 10 min at 97° C.; store at −20° C. until ready to use.

5. Hybridization, Scanning & STRIPPING

Figure 13:
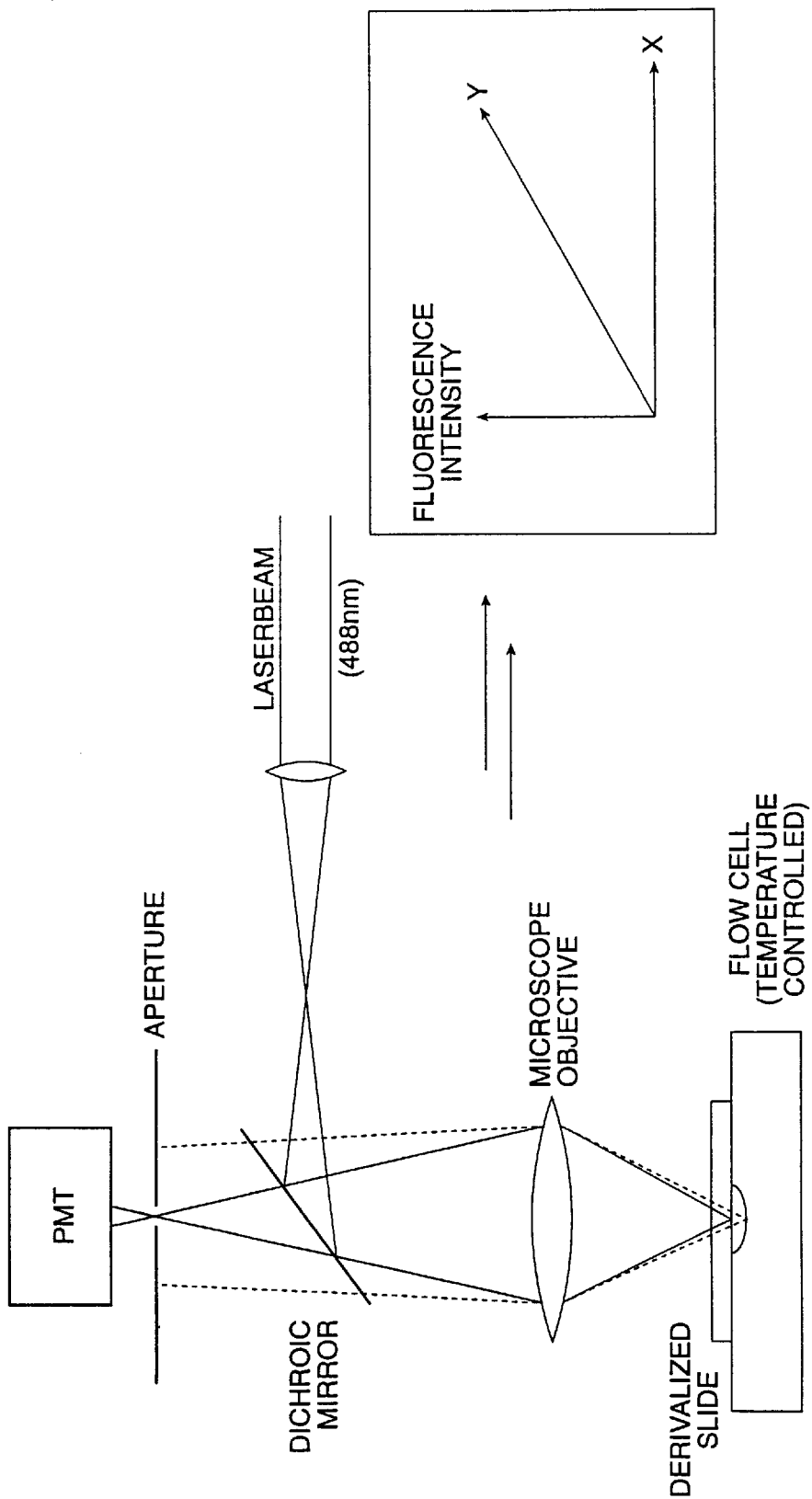
FIG. 13: Detection system for scanning a DNA chip.

A blank scan of the slide in hybridization buffer only is helpful to check that the slide is ready for use. The buffer is removed from the flow cell and replaced with 1 mL of (fragmented) DNA in hybridization buffer and mixed well. The scan is performed in the presence of the labeled target. FIG. 13 illustrates an illustrative detection system for scanning a DNA chip. A series of scans at 30 min intervals using a hybridization temperature of 25° C. yields a very clear signal, usually in at least 30 min to two hours, but it may be desirable to hybridize longer, i.e., overnight. Using a laser power of 50 μW and 50 μm pixels, one should obtain maximum counts in the range of hundreds to low thousands/pixel for a new slide. When finished, the slide can be stripped using 50% formamide. Rinsing well in deionized $H_2O$, blowing dry, and storing at room temperature.

C. Preparation of Labeled RNA/Hybridization to Array

1. Tagged primers

The primers used to amplify the target nucleic acid should have promoter sequences if one desires to produce RNA from the amplified nucleic acid. Suitable promoter sequences are shown below and include:

(1) the T3 promoter sequence:
5'-CGGAATTAACCCTCACTAAAGG
5'-AATTAACCCTCACTAAAGGGAG; (SEQ ID NO. 12)

(2) the T7 promoter sequence:
5' TAATACGACTCACTATAGGGAG (SEQ ID NO. 13); and (3) the SP6 promoter sequence:
5' ATTTAGGTGACACTATAGAA (SEQ ID NO. 14).

The desired promoter sequence is added to the 5' end of the PCR primer. It is convenient to add a different promoter to each primer of a PCR primer pair so that either strand may be transcribed from a single PCR product.

Synthesize PCR primers so as to leave the DMT group on. DMT-on purification is unnecessary for PCR but appears to be important for transcription. Add 25 μl 0.5M NaOH to collection vial prior to collection of oligonucleotide to keep the DMT group on. Deprotect using standard chemistry—55° C. overnight is convenient.

HPLC purification is accomplished by drying down the oligonucleotides, resuspending in 1 mL 0.1 M TEAA (dilute 2.0 M stock in deionized water, filter through 0.2 micron filter) and filter through 0.2 micron filter. Load 0.5 mL on reverse phase HPLC (column can be a Hamilton PRP-1 semi-prep, #79426). The gradient is 0→50% $CH_3CN$ over 25 min (program 0.2 μmol.prep.0–50, 25 min). Pool the desired fractions, dry down, resuspend in 200 μl 80% HAc. 30 min RT. Add 200 μl EtOH; dry down. Resuspend in 200 μl $H_2O$, plus 20 μl NaAc pH5.5, 600 μl EtOH. Leave 10 min on ice; centrifuge 12,000 rpm for 10 min in microfuge. Pour off supernatant. Rinse pellet with 1 mL EtOH, dry, resuspend in 200 μl H2O. Dry, resuspend in 200 μl TE. Measure A260, prepare a 10 pmol/μl solution in TE (10 mM Tris.Cl pH 8.0, 0.1 mM EDTA). Following HPLC purification of a 42 dt, a yield in the vicinity of 15 nmol from a 0.2 μmol scale synthesis is typical.

2. Genomic DNA Preparation

Add 500 μl (10 mM Tris.Cl pH8.0, 10 mM EDTA, 100 mM NaCl, 2% (w/v) SDS, 40 mM DTT, filter sterilized) to the sample. Add 1.25 μl 20 mg/ml proteinase K (Boehringer) Incubate at 55° C. for 2 hours, vortexing once or twice. Perform 2×0.5 mL 1:1 phenol:$CHCl_3$ extractions. After each extraction, centrifuge 12,000 rpm 5 min in a microfuge and recover 0.4 mL supernatant. Add 35 μl NaAc pH5.2 plus 1 mL EtOH. Place sample on ice 45 min; then centrifuge 12,000 rpm 30 min, rinse, air dry 30 min, and resuspend in 100 μl TE.

3. PCR

PCR is performed in a mixture containing, per reaction: 1 μl genomic DNA; 4 μl each primer (10 pmol/μl stocks); 4 μl 10×PCR buffer (100 mM Tris.Cl pH8.5, 500 mM KCl, 15 mM $MgCl_2$); 4 μl 2 mM dNTPs (made from 100 mM dNTP stocks); 1 U Taq polymerase (Perkin Elmer, 5 U/μl); $H_2O$ to 40 μl. About 40 cycles (94° C. 30 sec, 55° C. 30 sec, 72° C. 30 sec) are performed, but cycling conditions may need to be varied. These conditions are for 0.2 mL thin wall tubes in Perkin Elmer 9600. For products in the 200 to 1000 bp size range, check 2 μl of the reaction on a 1.5% 0.5×TBE agarose gel using an appropriate size standard. For larger or smaller volumes (20–100 μl), one can use the same amount of genomic DNA but adjust the other ingredients accordingly.

4. In vitro transcription

Mix: 3 μl PCR product; 4 μl 5×buffer; 2 μl DTT; 2.4 μl 10 mM rNTPs (100 mM solutions from Pharmacia); 0.48 μl 10 mM fluorescein-UTP (Fluorescein-12-UTP, 10 mM solution, from Boehringer Mannheim); 0.5 μl RNA polymerase (Promega T3 or T7 RNA polymerase); and add $H_2O$ to 20 μl. Incubate at 37° C. for 3 h. Check 2 μl of the reaction on a 1.5% 0.5×TBE agarose gel using a size standard. 5×buffer is 200 mM Tris pH 7.5, 30 mM $MgCl_2$, 10 mM spermidine, 50 mM NaCl, and 100 mM DTT (supplied with enzyme). The PCR product needs no purification and can be added directly to the transcription mixture. A 20 μl reaction is suggested for an initial test experiment and hybridization; a 100 μl reaction is considered "preparative" scale (the reaction can be scaled up to obtain more target). The amount of PCR product to add is variable; typically a PCR reaction will yield several picomoles of DNA. If the PCR reaction does not produce that much target, then one should increase the amount of DNA added to the transcription reaction (as well as optimize the PCR). The ratio of fluorescein-UTP to UTP suggested above is 1:5, but ratios from 1:3 to 1:10—all work well. One can also label with biotin-UTP and detect with streptavidin-FITC to obtain similar results as with fluorescein-UTP detection.

For nondenaturing agarose gel electrophoresis of RNA, note that the RNA band will normally migrate somewhat faster than the DNA template band, although sometimes the two bands will comigrate. The temperature of the gel can effect the migration of the RNA band. The RNA produced from in vitro transcription is quite stable and can be stored for months (at least) at −20° C. without any evidence of degradation. It can be stored in unsterilized 6×SSPE 0.1% triton X-100 at −20° C. for days (at least) and reused twice (at least) for hybridization, without taking any special precautions in preparation or during use. RNase contamination should of course be avoided. When extracting RNA from cells, it is preferable to work very rapidly and to use strongly denaturing conditions. Avoid using glassware previously contaminated with RNases. Use of new disposable plasticware (not necessarily sterilized) is preferred, as new plastic tubes, tips, etc., are essentially RNase free. Treatment with DEPC or autoclaving is typically not unnecessary.

5. Fragmentation

In a 0.2 mL thin-wall PCR tube mix: 18 μl RNA (direct from transcription reaction—no purification required); 18 μl $H_2O$; and 4 μl 1 M Tris.Cl pH9.0. Incubate at 99.9° C. for 60 min. Add to 1 mL hybridization buffer and store at −20° C. until ready to use. The alkaline hydrolysis step is very reliable. The hydrolysed target can be stored at −20° C. in 6×SSPE/0.1% Triton X-100 for at least several days prior to use and can also be reused.

6. Hybridization, Scanning, & STRIPPING

A blank scan of the slide in hybridization buffer only is helpful to check that the slide is ready for use. The buffer is removed from the flow cell and replaced with 1 mL of (hydrolysed) RNA in hybridization buffer and mixed well. Incubate for 15–30 min at 18° C. Remove the hybridization solution, which can be saved for subsequent experiments. Rinse the flow cell 4–5 times with fresh changes of 6×SSPE/0.1% Triton X-100, equilibrated to 18° C. The rinses can be performed rapidly, but it is important to empty the flow cell before each new rinse and to mix the liquid in the cell thoroughly. The scan is performed in the presence of the labeled target. A series of scans at 30 min intervals using a hybridization temperature of 25° C. yields a very clear signal, usually in at least 30 min to two hours, but it may be desirable to hybridize longer, i.e., overnight. Using a laser power of 50 μW and 50 μm pixels, one should obtain maximum counts in the range of hundreds to low thousands/ pixel for a new slide. When finished, the slide can be stripped using 50% to 100% formamide at 50° C. for 30 min, rinsing well in deionized H₂O, blowing dry, and storing at room temperature.

These conditions are illustrative and assume a probe length of ~15 nucleotides. The stripping conditions suggested are fairly severe, but some signal may remain on the slide if the washing is not stringent. Nevertheless, the counts remaining after the wash should be very low in comparison to the signal in presence of target RNA. In some cases, much gentler stripping conditions are effective. The lower the hybridization temperature and the longer the duration of hybridization, the more difficult it is to strip the slide. Longer targets may be more difficult to strip than shorter targets.

7. Amplification of Signal

A variety of methods can be used to enhance detection of labelled targets bound to a probe on the array. In one embodiment, the protein MutS (from *E. coli*) or equivalent proteins such as yeast MSH1, MSH2, and MSH3; mouse Rep-3, and Streptococcus Hex-A, is used in conjunction with target hybridization to detect probe-target complex that contain mismatched base pairs. The protein, labeled directly or indirectly, can be added to the chip during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues.

8. Detection of Repeat Sequences

In some circumstances, i.e., target nucleic acids with repeated sequences or with high G/C content, very long probes are sometimes required for optimal detection. In one embodiment for detecting specific sequences in a target nucleic acid with a DNA chip, repeat sequences are detected as follows. The chip comprises probes of length sufficient to extend into the repeat region varying distances from each end. The sample, prior to hybridization, is treated with a labelled oligonucleotide that is complementary to a repeat region but shorter than the full length of the repeat. The target nucleic is labelled with a second, distinct label. After hybridization, the chip is scanned for probes that have bound both the labelled target and the labelled oligonucleotide probe; the presence of such bound probes shows that at least two repeat sequences are present.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

---

What is claimed is:

1. An array of oligonucleotide probes immobilized on a solid support, the array having at least four sets of oligonucleotide probes at least 9 nucleotides in length, (1) a first probe set having a probe corresponding to each nucleotide in a reference sequence from a human immunodeficiency virus, each probe being exactly complementary to a subsequence of the reference sequence that includes the corresponding nucleotide and each probe having an interrogation position occupied by a complementary nucleotide to the corresponding nucleotide, (2) three additional probe sets, each of which has a corresponding probe for each probe in the first probe set, the three corresponding probes in the three additional probe sets being identical to the corresponding probe from the first probe set or a subsequence thereof that includes the interrogation position, except that the interrogation position is occupied by a different nucleotide in each of the four corresponding probes;

provided the array lacks a complete set of oligonucleotide probes of a given length.

2. The array of claim 1, wherein the reference sequence is from a reverse transcriptase gene of the human immunodeficiency virus.

3. The array of claim 2, wherein the reference sequence is a full-length reverse transcriptase gene.

4. The array of claim 2 having at least 3200 oligonucleotide probes.

5. The array of claim 4, wherein the array has at least 10,000 oligonucleotide probes.

6. The array of claim 5, wherein the HIV gene is from the BRU HIV strain.

7. The array of claim 5, wherein the HIV gene is from the SF2 HIV strain.

8. The array of claim 1, wherein the array further comprises fifth, sixth, seventh and eighth probe sets, (1) the fifth probe set having a probe corresponding to each nucleotide in a second reference sequence, each probe being exactly complementary to a subsequence of the second reference sequence that includes the corresponding nucleotide from the second reference sequence, and each probe having an interrogation position occupied by a complementary nucleotide to the corresponding nucleotide in the second reference sequence, and (2) the sixth, seventh, and eight probe sets, each having a corresponding probe for each probe in the fifth probe set, the three corresponding probes in the sixth, seventh, and eighth probe sets being identical to the corresponding probe from the fifth probe set or a subsequence thereof that includes the interrogation position, except that the interrogation position is occupied by a different nucleotide in each of the four corresponding probes from the fifth, sixth, seventh and eighth probe sets.

9. The array of claim 8, wherein the reference sequence is from the coding strand of the reverse transcriptase gene and the second reference sequence is from the noncoding strand of the reverse transcriptase gene.

10. The array of claim 8, wherein the first, second, third and fourth probe sets have probes of a first length and the fifth, sixth, seventh and eight probe sets have probes of a second length different from the first length.

11. The array of claim 8, wherein the second reference sequence comprises a subsequence of the first reference sequence with a substitution of at least one nucleotide.

12. The array of claim 11, wherein the substitution confers drug resistance to a human immunodeficiency virus comprising the second reference sequence.

13. The array of claim 8, wherein the second reference sequence is from a reverse transcriptase gene of a second strain of a human immunodeficiency virus.

14. The array of claim 8, wherein the second reference sequence is from a 16S RNA, or DNA encoding the 16S RNA, from a pathogenic microorganism.

15. A method of comparing a target nucleic acid from a human immunodeficiency virus with a reference sequence from a second human immunodeficiency virus having a predetermined sequence of nucleotides, the method comprising:

(a) hybridizing the target nucleic acid to an array of oligonucleotide probes immobilized on a solid support, the array comprising oligonucleotide probes at least 9 nucleotides in length, the oligonucleotide probes comprising at least four sets of probes, (1) the first probe set having a probe corresponding to each nucleotide in a reference sequence, each probe being exactly complementary to a subsequence of the reference sequence that includes the corresponding nucleotide, and each probe having an interrogation position occupied by a complementary nucleotide to the corresponding nucleotide in the reference sequence, and (2) three additional probe sets, each of which has a corresponding probe for each probe in the first probe set, the three corresponding probes in the three additional probe sets being identical to the corresponding probe from the first probe set or a subsequence thereof that includes the interrogation position, except that the interrogation position is occupied by a different nucleotide in each of the four corresponding probes (b) comparing the relative specific binding of four corresponding probes from the first, second, third and fourth probe sets to determine the identity of the corresponding nucleotide in the target sequence, (c) repeating (b) by comparing the relative specific binding of a further four corresponding probes until the identity of each nucleotide of interest in the target sequence has been determined thereby indicating whether the target sequence is the same or different from the reference sequence.

16. The method of claim 15, wherein the target sequence is from the reverse transcriptase gene of the human immunodeficiency virus and the reference sequence is from the reverse transcriptase gene of second immunodeficiency virus.

17. The method of claim 16, wherein the target sequence has a substituted nucleotide relative to the reference sequence in at least one undetermined position, and the comparing step indicates the identity of the nucleotide occupying the position in the target sequence.

18. The method of claim 16, wherein the target sequence has a substituted nucleotide relative to the reference sequence in at least one position, the substitution conferring drug resistance to the human immunodeficiency virus, and the comparing step indicates the identity of the substituted nucleotide.

19. The method of claim 16, wherein:

the hybridizing step comprises hybridizing the target nucleic acid and a second target nucleic acid, the second target sequence being from a reverse transcriptase gene of a third human immunodeficiency virus to the array; and the relative specific binding of four corresponding probes from the first, second, third and fourth probe sets further determines the identity of a corresponding nucleotide in the second target sequence.

20. The method of claim 19, wherein the first target sequence has a first label and the second target sequence has a second label different from the first label.

21. The method of claim 20, wherein undetermined first and second proportions of the first and second target sequences are hybridized to the array and the relative specific binding of the four corresponding probes from the first, second, third and fourth probe sets further indicates the proportions.

22. The array of claim 1, having up to 100,000 probes.

23. The array of claim 1, wherein the reference sequence is at least 50 nucleotides long.

24. The array of claim 1, wherein the first probe set comprises a series of overlapping probes spanning the reference sequence.

25. The array of claim 1, wherein the probes are 9 to 21 nucleotides in length.

26. The method of claim 15, wherein the probes are 9 to 21 nucleotides length.

* * * * *